United States Patent
Ainge et al.

(10) Patent No.: US 8,227,622 B2
(45) Date of Patent: Jul. 24, 2012

(54) PHARMACEUTICAL PROCESS AND INTERMEDIATES 714

(75) Inventors: Debra Ainge, Leicestershire (GB); Eric Merifield, Leicestershire (GB); Colin Thomson, Leicestershire (GB); Michael Butters, Bristol (GB); Ravi Ramakrishnan, Bangalore (IN); Ravi Naidu Rayapati, Bangalore (IN); Parhalad Ray Sharma, Bangalore (IN)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 12/830,577

(22) Filed: Jul. 6, 2010

(65) Prior Publication Data

US 2011/0046394 A1 Feb. 24, 2011

Related U.S. Application Data

(60) Provisional application No. 61/223,163, filed on Jul. 6, 2009.

(51) Int. Cl.
*C07D 209/30* (2006.01)
*C07D 209/12* (2006.01)

(52) U.S. Cl. .................................... 548/516
(58) Field of Classification Search .............. None
See application file for complete search history.

(56) References Cited

U.S. PATENT DOCUMENTS

| | | | |
|---|---|---|---|
| 6,916,841 B2 | 7/2005 | Seehra et al. | |
| 6,933,316 B2 | 8/2005 | Hsieh et al. | |
| 7,687,535 B2 | 3/2010 | Bonnert et al. | |
| 7,709,521 B2 | 5/2010 | Bonnert et al. | |
| 7,723,373 B2 | 5/2010 | Bonnert et al. | |
| 7,741,360 B2 | 6/2010 | Bonnert et al. | |
| 7,754,735 B2 | 7/2010 | Birkinshaw et al. | |
| 7,781,598 B2 | 8/2010 | Keegan et al. | |
| 2006/0111426 A1 | 5/2006 | Bonnert et al. | |
| 2008/0051586 A1 | 2/2008 | Keegan et al. | |
| 2008/0249110 A1 | 10/2008 | Bonnert et al. | |
| 2009/0163518 A1 | 6/2009 | Bonnert et al. | |
| 2010/0197756 A1 | 8/2010 | Bonnert et al. | |
| 2011/0263614 A1 | 10/2011 | Bonnert et al. | |

FOREIGN PATENT DOCUMENTS

| | | |
|---|---|---|
| GB | 2422831 | 8/2006 |
| WO | WO 01/32621 | 5/2001 |
| WO | WO 2004/007451 | 1/2004 |
| WO | WO2004/106302 | 12/2004 |
| WO | WO 2004106302 A1 * | 12/2004 |
| WO | WO2006/067416 | 6/2006 |
| WO | WO2006/075138 | 7/2006 |
| WO | WO2006/075139 | 7/2006 |
| WO | WO 2007/140786 | 12/2007 |
| WO | WO 2008/000409 | 1/2008 |

OTHER PUBLICATIONS

Nagarajan et al. "Synthesis & Oral Hypoglycemic Properties of 4-Oxo-4,5,6,7-tetrahydro-indole-3-acetic Acids" Indian J. Chem. 1988 (278) 1113-1123.
Newman et al. "An Improved Aromatization of α-Tetralone Oximes to *N*-(1-Naphthyl)acetamides" J. Org. Chem. 1973 (38) 4073-4074.
Piras et al. "Scaffold Preparation and Parallel Synthesis of Arrays of 5,6,7,8-Tetrahydropyrrolo-azepinones in the Solution Phase" Eur. J. Org. Chem. 2008 2789-2800.
Strasser et al. "Design and Synthesis of 5-Lipoxygenase Inhibitors" Helvetica Chimica Acta. 1988 (71) 1156-1176.
Birkinshaw et al., "Discovery of potent CRTh2 ($DP_2$) receptor antagonists", *Bioorganic & Medicinal Chemistry Letters* 16:4287-4290 (2006).
Bonnert, R. "Generation of selective CRTh2 antagonists from distinct chemical series", Congress; Pacifichem 2010 Conference in Honolulu (abstract).
Carrillo et al., "Pharmacological characterisation of dog recombinant CRTh2", *Proceedings of the British Pharmacological Society* Winter meeting 2005; 3(4):102P available online at http://www.pA2online.org/abstracts/Vol3Issue4abst102P.pdf (abstract).
Carrillo et al., "Pharmacological Characterisation of Recombinant Dog CRTh2", *Proceedings of the American Thoracic Society* May 2006 meeting, Am J Respir Crit Care Med 2006; 3 (Abstract Issue): A584.
Damasio A. R., Alzheimer's Disease and Related Dementias, Cecil Textbook of Medicine, 20th edition, vol. 2:1992-1996 (1996).
Damasio A. R., Alzheimer's Disease and Related Dementias, Cecil Textbook of Medicine, 20th edition, vol. 2:2050-2057 (1996).

(Continued)

*Primary Examiner* — Yong Chu
*Assistant Examiner* — Michael Barker
(74) *Attorney, Agent, or Firm* — Fish & Richardson P.C.

(57) ABSTRACT

The invention relates to compounds of formula (X), and salts thereof, and their use as intermediates in improved manufacturing processes for the synthesis of pharmaceutical compound (I):

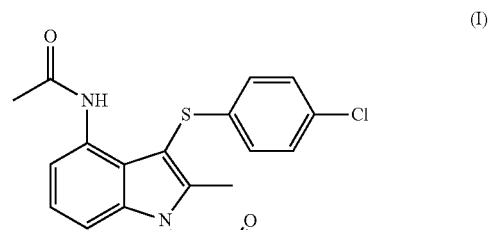

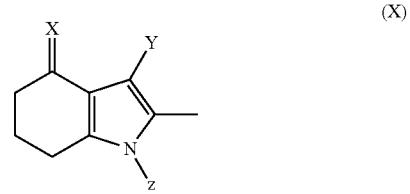

X is =O, =N—OH or =N—OC(O)Me; Y is hydrogen, PhS- or p-chlorophenylsulfanyl; Z is hydrogen or —$CH_2COOR^1$ wherein $R^1$ is selected from hydrogen, optionally substituted hydrocarbyl and optionally substituted heterocyclyl.

22 Claims, No Drawings

OTHER PUBLICATIONS

FDA mulls drug to slow late-stage Alzheimer's [online], [retrieved on Sep. 23, 2003]. Retrieved from the Internet, URL:http://www.cnn.com/2003/HEALTH/conditions/09/24/alzheimers.drug.ap/indexhtml, pp. 1 and 2.

Luker et al., "Generation of Selective CRTh2 Antagonists from Distinct Chemical Series" slides presented in Pacifichem 2010 Conference in Honolulu (36 pages).

Lüscher et al., "Deblocking of o-Nitrophenylsulfenyl-Protected Peptides by Ammonium Thiocyanate and (2-Methyl-1-indolyl) acetic acid", *Helv. Chim. Acta* 66(2):602-605 (1983).

Marshall et al., "Functional Effects of CRTh2 in the Dog", *Proceedings of the American Thoracic Society* May 2006 meeting, Am J Respir Crit Care Med 2006; 3 (Abstract Issue): A584.

Marshall et al., "Is there a CRTh2 functional response in the dog?", *Proceedings of the British Pharmacological Society* Winter meeting 2005; 3(4):103P available online at http://www.pA2online org/abstracts/Vol3Issue4abst103P.pdf (abstract).

Morissette et al., "High-throughput crystallization: polymorphs, salts, co-crystals and solvates of pharmaceutical solids", *Advanced Drug Delivery Reviews* 56:275-300 (2004).

Patani and LaVoie, "Bioisosterism: A Rational Approach in Drug Design", *Chem Rev.* 96:3147-3176 (1996).

Royer et al., "A novel antagonist of prostaglandin $D_2$ blocks the locomotion of eosinophils and basophils", *Eur J Clin Invest* 38(9):663-671 (2008).

Sargnet et al., "The effect of a selective CRTh2 antagonist on tobacco smoke (TS) induced inflammation and remodelling in the mouse", *Proceedings of the British Pharmacological Society* $7^{th}$ James Black Conference 2009; 003P at http://www.pA2onlne.org/abstracts/Vol7Issue3abst003P.pdf (abstract).

STN International, CAPLUS accession No. 2001:338492, Document No. 134:353315, Wakunaga Pharmaceutical Co., Ltd., "Preparation of indole derivatives as chymase inhibitors and drugs containing the same as the active ingredient", & WO,A1,2001032621, 20010510, RN 64137-76-4, 336186-33-5, (2001).

Vippagunta et al., abstract, "Crystalline solids", *Advanced Drug Delivery Reviews* 48:3-26 (2001).

USPTO Non-Final Office Action in U.S. Appl. No. 10/521,325, mailed Jan. 9, 2007, 32 pages.

Fish & Richardson P.C., Amendment in Reply to Action of Jan. 9, 2007 in U.S. Appl. No. 10/521,325, filed Jul. 9, 2007, 15 pages.

USPTO Final Office Action in U.S. Appl. No. 10/521,325, mailed Oct. 15, 2007, 6 pages.

Fish & Richardson P.C., RCE/IDS and Amendment in Reply to Action of Oct. 15, 2007 in U.S. Appl. No. 10/521,325, filed Feb. 21, 2008, 13 pages.

USPTO Non-Final Office Action in U.S. Appl. No. 10/521,325, mailed May 1, 2008, 35 pages.

Fish & Richardson P.C., Amendment in Reply to Action of May 1, 2008 in U.S. Appl. No. 10/521,325, filed Aug. 1, 2008, 10 pages.

USPTO Non-Final Office Action in U.S. Appl. No. 10/521,325, mailed Nov. 14, 2008, 8 pages.

Fish & Richardson P.C., Amendment in Reply to Action of Nov. 14, 2008 in U.S. Appl. No. 10/521,325, filed Mar. 13, 2009, 14 pages.

USPTO Final Office Action in U.S. Appl. No. 10/521,325, mailed Jul. 9, 2009, 9 pages.

Fish & Richardson P.C., RCE/IDS and Amendment in Reply to Action of Jul. 9, 2009 in U.S. Appl. No. 10/521,325, filed Oct. 9, 2009, 14 pages.

USPTO Notice of Allowance in U.S. Appl. No. 10/521,325, mailed Jan. 12, 2010, 9 pages.

Fish & Richardson P.C., Response to Notice of Allowance of Jan. 12, 2010 in U.S. Appl. No. 10/521,325, filed Apr. 9, 2010, 2 pages.

USPTO Non-Final Office Action in U.S. Appl. No. 12/758,348, mailed Jan. 28, 2011, 17 pages.

Fish & Richardson P.C., Amendment in Reply to Office Action of Jan. 28, 2011 in U.S. Appl. No. 12/758,348, filed May 2, 2011, 16 pages.

USPTO Final Office Action in U.S. Appl. No. 12/758,348, mailed Jul. 18, 2011, 11 pages.

USPTO Restriction Requirement in U.S. Appl. No. 10/558,228, mailed Sep. 19, 2008, 9 pages.

Fish & Richardson P.C., Response to Restriction Requirement of Sep. 19, 2008 in U.S. Appl. No. 10/558,228, filed Oct. 17, 2008, 6 pages.

USPTO Non-Final Office Action in U.S. Appl. No. 10/558,228, mailed Jan. 9, 2009, 25 pages.

Fish & Richardson P.C., Amendment in Reply to Action of Jan. 9, 2009 in U.S. Appl. No. 10/558,228, filed Mar. 5, 2009, 9 pages.

USPTO Notice of Allowance in U.S. Appl. No. 10/558,228, mailed May 19, 2009, 8 pages.

Fish & Richardson P.C., RCE/IDS in reply to Notice of Allowance of May 19, 2009 in U.S. Appl. No. 10/558,228, filed Aug. 19, 2009, 5 pages.

USPTO Notice of Allowance in U.S. Appl. No. 10/558,228, mailed Nov. 3, 2009, 8 pages.

Fish & Richardson P.C., Response to Notice of Allowance of Nov. 3, 2009 in U.S. Appl. No. 10/558,228, filed Feb. 2, 2010, 2 pages.

USPTO Non-Final Office Action in U.S. Appl. No. 12/397,618, mailed Dec. 14, 2010, 17 pages.

Baldwin et al. "Stereoelectronic Control in Organic Chemistry: Addition Reactions of Some 1,4-Benzoquinone 4-(O-Methyloximes)" J. Org. Chem. 1981 (46) 697-703.

Barraja et al. "Pyrrolo[2,3-h]quinolinones: Synthesis and Photochemotherapic Activity" Bioorg. Med. Chem. Lett. 2003 (13) 2809-2811.

Bergman et al. "A New Versatile Synthesis of 4-Nitroindoles", Tetrahedron Letters 1983 24(34) 3665-3668.

Bergman et al. "Synthesis of Indoles via Ring Closure of 2-Alkylnitroaniline Derivatives" Tetrahedron 1990 46(17) 6085-6112.

Calder et al. "Synthesis and Reactions of Some para-Substituted N-Hydroxyacetanilides" Aust. J. Chem. 1979 (32) 1301-1306.

Chacón-García et al. "Synthesis and in vitro cytotoxic activity of pyrrolo[2,3-e]indole derivatives and a dihydro benzoindole analogue" Eur. J. Med. Chem. 2002 (37) 261-266.

Danish et al. "Reduction of 1-Hydroxyimino-1,2,3,4-tetrahydrocarbazoles by Metal and Baker's Yeast—Syntheses of Aminocarbazole Derivatives" Z. Naturforsch. 2004 (59b) 1054-1058.

Golub et al. "Molecular Classification of Cancer: Class Discovery and Class Prediction by Gene Expression Monitoring" Science 1999 (286) 531-537.

Hall et al. "The kinetics and mechanism of the reaction of tricoordinate phosphorus compounds with sulfenate esters" Phosphorus, Sulfur Silicon 1997 (123) 341-358.

Lala et al. "Role of nitric oxide in tumor progression: Lessons from experimental tumors" Cancer and Metastasis Reviews 1998 (17) 91-106.

Meinhold et al. "Cyclofunctionalization of 2-Allyl-phenols with Sulfur Chlorides. Iii. 2-Arylthiomethyl-2,3-dihydrofuro [3,2 -h]quinolins from 7-Allyl- and 7-Methallyl-8-hydroxyquinoline, respectively, and Arylsulfenyl Chlorides" Journal f. prakt. Chemie. Band 1989 (331) S136-140 Abstract.

Moskalev et al. "A Novel Method of Indole Ring System Construction: One-Pot Synthesis of 4- and 6-Nitroindole Derivatives via Base Promoted Reaction Between 3-Nitroaniline and Ketones" Tetrahedron Letters 1999 (40) 5395-5398.

Moskalev et al. "Synthesis of 4- and 6-substituted nitroindoles" Tetrahedron 2004 (60) 347-358.

Tamura et al. "A Synthesis of 5-Amino- and 5-Hdroxy-l-ethyl-1,4-dihydrio-4-oxo-3-quinolinecarboxylic Acids and Their Derivatives" J. Heterocycl Chem. 1982 (19) 289-296.

Theobald et al. "Stereospecific Reductive Desulfurization of Vinyl Sulfoxides with tert-Butyllithium and an Internal Proton Source" J. Org. Chem. 1990 (55) 741-750.

USPTO Non-Final Office Action in U.S. Appl. No. 13/047,280, mailed Oct. 5, 2011, 22 pages.

* cited by examiner

PHARMACEUTICAL PROCESS AND INTERMEDIATES 714

The present invention relates to the technical field concerned with the large-scale manufacture of pharmaceutical compounds.

CROSS-REFERENCE TO RELATED APPLICATIONS

This application claims the benefit under 35 U.S.C. §119 (e) of Application No. 61/223,163 (US), filed on 6 Jul. 2009, which is incorporated herein by reference in its entirety.

International patent application PCT/SE2004/000808, (WO2004/106302) is concerned with substituted indoles useful as pharmaceutical compounds for treating respiratory disorders, pharmaceuticals containing them and processes for their preparation. More specifically, page 25 of WO2004/106302 discloses 4-(acetylamino)-3-[(4-chloro-phenyl) thio]-2-methyl-1H-indole-1-acetic acid, (hereafter referred to as the compound of formula (I)) as Example 1.

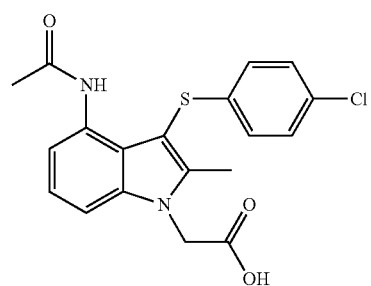

The route disclosed on pages 25 and 26 of WO2004/106302 for the preparation of the compound of formula (I) is shown in Scheme (I), below.

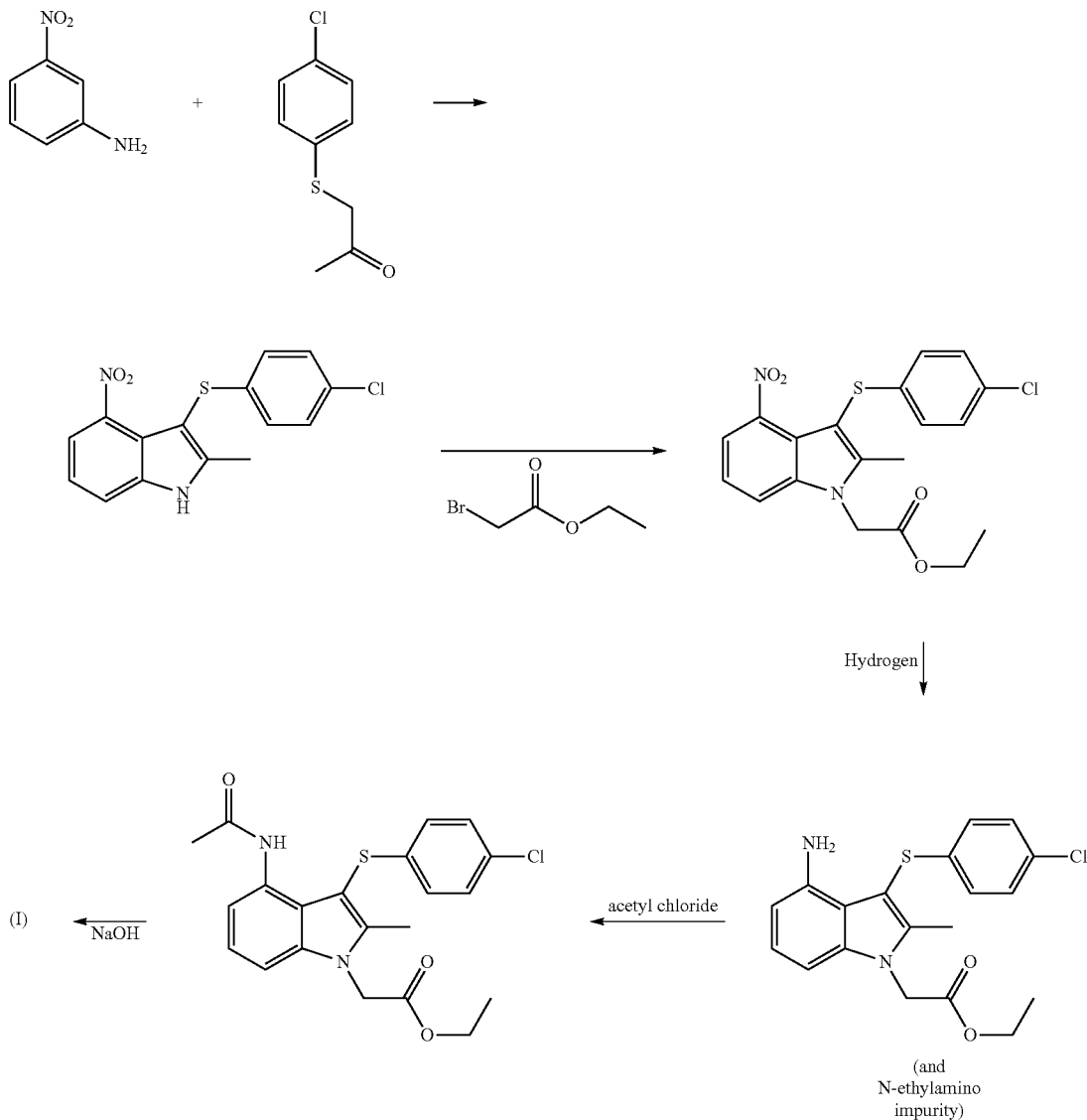

The synthesis of the compound of formula (I) disclosed in WO2004/106302 has a number of potential disadvantages.

For example, the prior art process involves the use of very low temperatures (−78° C.). Such low temperatures can be difficult to achieve on large scale, requiring specialist plant equipment and a lot of energy.

The prior art process involves the use of tert-butyl hypochlorite, which is seen as undesirable for a large-scale manufacturing process.

The prior art process involves the use of dichloromethane, which is an undesirable solvent for large-scale use because of its environmental impact.

The present inventors have established that one or more of the prior art reactions occur relatively quickly. Fast exothermic reactions can be disadvantageous for larger scale manufacture in a batch mode because of the need to control and adequately remove the heat evolved.

International patent application PCT/GB2006/000060, (WO2006/075139) is concerned with a novel process for the preparation of substituted indoles that are useful as therapeutic agents. More specifically, WO2006/075139 discloses processes for the preparation of the compound of formula (I), where each process starts from 2-methyl-4-nitroindole.

The synthesis of the compound of formula (I) disclosed in WO2006/075139 has a number of disadvantages.

There is evidence to suggest that 2-methyl-4-nitroindole is not a good starting material for use in a large-scale manufacturing process. One of the methods known for the synthesis of 2-methyl-4-nitroindole appears to provide a low yield of the desired product (*Tetrahedron*, 1990, 46(17), 6085; and *Tetrahedron Letters*, 1983, 24(34), 3665-8). Another known method of synthesis of 2-methyl-4-nitroindole requires conditions that are undesirable for larger-scale synthesis because it involves the use of an atmosphere of air in the presence of organic solvents which may present control and safety difficulties. (*Tetrahedron Letters*, 1999, 40, 5395; and *Tetrahedron*, 2004, 60, 347). Indeed, 2-methyl-4-nitroindole itself has been found to be a highly energetic molecule (positive result in a Koenen tube test at 2 mm), a significant hurdle to its use on large scale. Furthermore, 2-methyl-4-nitroindole has been found to be relatively expensive as a starting material, partly due to the large solvent volumes required and the need for multiple crystallisations to remove by products. Therefore the "cost of goods" for the prior art syntheses of the compound of formula (I) from 2-methyl-4-nitroindole is potentially disadvantageously high.

The compound of formula (I) is being developed as an active pharmaceutical compound. Appropriate methods for safe, cost-effective, efficient and environmentally sensitive manufacture of the compound of formula (I) are therefore desirable.

The present invention provides a solution to one or more of the above-mentioned disadvantages. Additional technical advantages of different aspects of the invention are described herein below.

In the first aspect of the invention there is provided a compound of formula (X):

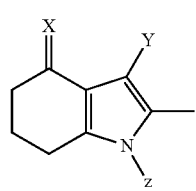

(X)

wherein:
X is =O, =N—OH or =N—OC(O)Me;
Y is hydrogen or

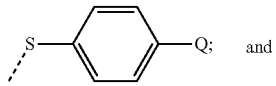

and

Q is hydrogen or chloro;
and Z is hydrogen or —CH$_2$COOR$^1$ where in R$^1$ is selected from hydrogen, optionally substituted hydrocarbyl and optionally substituted heterocyclyl;
or a salt thereof.

In a further aspect there is provided a compound of formula (X) as defined herein.

In yet a further aspect of the invention there is provided a compound of formula (II):

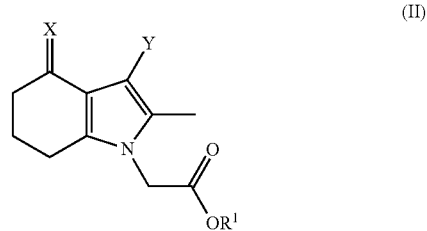

(II)

wherein:
R$^1$ is selected from hydrogen, optionally substituted hydrocarbyl and optionally substituted heterocyclyl;
X is =O, =N—OH or =N—OC(O)Me;
Y is hydrogen or

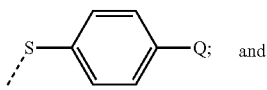

and

Q is hydrogen or chloro;
or a salt thereof.

Surprisingly the inventors have found that the pharmaceutical compound of formula (I) may be prepared efficiently on large scale from the compound of formula (X) even though the compound of formula (X) does not even contain the core benzene ring that is ultimately present in the compound of formula (I).

In a further aspect there is provided the use of the compound of formula (II), or a salt thereof, as defined herein, as a pharmaceutical intermediate.

In one embodiment there is provided the use of the compound of formula (II), or a salt thereof, as defined herein, as an intermediate for the manufacture of the compound of formula (I), or a salt thereof.

In a further aspect there is provided a compound of formula (II) as defined herein.

The skilled person will appreciate that a wide range of R$^1$ groups may be used for carrying out the present invention since the R$^1$ group is only a temporary feature that is not expected to play a key part in the process of the present invention. It is to be understood that the R$^1$ group may be removed using basic conditions, to release R$^1$OH and the compound of formula (I), or a salt thereof. In certain cases the R$^1$ group may be cleaved under acidic conditions or using hydrogen gas with a hydrogenation catalyst or using other established conditions for cleavage of a given type of ester group. The skilled person understands which of the aforementioned conditions might be preferable depending on the nature of the R¹ group.

Alternative embodiments and values of variable groups are described below, and it is to be understood that such variable groups in any aspect or embodiment may be combined with any other variable groups or aspect or embodiment described hereinbefore or hereinafter. Embodiments and aspects of the invention encompass all such combinations of variable groups.

In one embodiment there is provided a compound of formula (II) of formula (IIa):

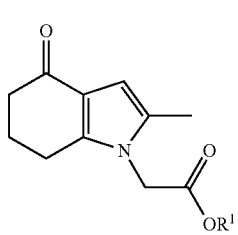

(IIa)

wherein R¹ is selected from hydrogen, optionally substituted hydrocarbyl and optionally substituted heterocyclyl; or a salt thereof.

In one embodiment there is provided the use of a compound of formula (II) of formula (IIa), or a salt thereof, as defined herein, as a pharmaceutical intermediate.

In one embodiment there is provided the use of a compound of formula (II) of formula (IIa), or a salt thereof, as defined herein, as an intermediate for the manufacture of the compound of formula (I), or a salt thereof.

The compound of formula (IIa) may be prepared by reacting a compound of formula (III):

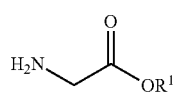

(III)

with 2-(2-oxopropyl)cyclohexane-1,3-dione; wherein the values of R¹ are as defined herein.

2-(2-Oxopropyl)cyclohexane-1,3-dione is a known compound, and may be prepared using cyclohexane-1,3-dione and chloroacetone under basic conditions, as described hereinafter.

The compound of formula (III) is either commercially available or it may be prepared using well-known chemistry from commercially available starting materials. For example the NH₂-group of the compound of formula (III) may be introduced via displacement of a halo group from a 2-haloacetate ester, for example ethyl 2-chloroacetate. The skilled person understands and that the use of a nitrogen protecting group may be beneficial for such a transformation.

Alternatively N-protected glycine may be coupled to an alcohol of formula R¹OH using a coupling agent such as EDCI or using other esterification conditions that are well known in the art.

The compound of formula (IIa) may be converted into the compound of formula (I) by carrying out the following transformations:

when R¹ is hydrogen:
(i) esterification—incorporating the R¹ group;
and then in all cases:
(ii) thioarylation—incorporating the thioaryl group;
(iii) acetylation and aromatisation—creating the core benzene ring and incorporating the acetyl group;
and subsequently:
(iv) deprotection (de-esterification)—removing the R¹ group;
wherein steps (ii) and (iii) may be performed in either order.

In one embodiment there is provided a compound of formula (II) of formula (IIb):

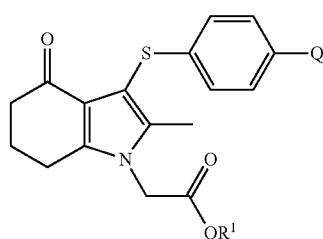

(IIb)

wherein R¹ is selected from hydrogen, optionally substituted hydrocarbyl and optionally substituted heterocyclyl; or a salt thereof In one embodiment there is provided the use of a compound of formula (II) of formula (IIb), or a salt thereof, as defined herein, as a pharmaceutical intermediate.

In one embodiment there is provided the use of a compound of formula (II) of formula (IIb), or a salt thereof, as defined herein, as an intermediate for the manufacture of the compound of formula (I), or a salt thereof.

The compound of formula (IIb) may be prepared by reacting a compound of formula (IIa) as defined herein, with a compound of formula (IVa) or (IVb):

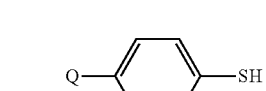

(IVa)

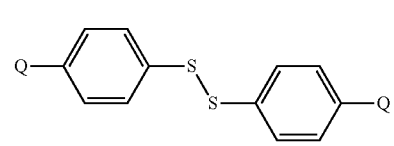

(IVb)

using a halogenating agent to activate the reactant or to convert to the sulfenyl halide. For example a chlorinating agent may be used. Examples of suitable chlorinating agents include trichloroisocyanuric acid (TCCA), sulphuryl chloride and chlorine.

The compound of formula (IIa) may be converted into the compound of formula (I) by carrying out the following transformations:
when R¹ is hydrogen:
(i) esterification—incorporating an R¹ group;
and then in all cases:
(ii) acetylation and aromatisation—creating the core benzene ring and incorporating the acetyl group;
and subsequently:
(iii) deprotection (i.e. de-esterification)—removing the R¹ group.

In one embodiment there is provided a compound of formula (II) of formula (IIc):

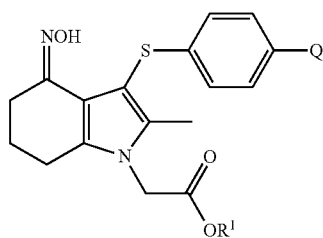

(IIc)

wherein R¹ is selected from hydrogen, optionally substituted hydrocarbyl and optionally substituted heterocyclyl; or a salt thereof.

In one embodiment there is provided the use of a compound of formula (II) of formula (IIc), or a salt thereof, as defined herein, as a pharmaceutical intermediate.

In one embodiment there is provided the use of a compound of formula (II) of formula (IIc), or a salt thereof, as defined herein, as an intermediate for the manufacture of the compound of formula (I), or a salt thereof.

The compound of formula (IIc) may be prepared by reacting a compound of formula (IIb) with hydroxylamine or a salt thereof, for example hydroxylamine hydrochloride.

The compound of formula (IIc) may be converted into the compound of formula (I) by carrying out the following transformations:
when R¹ is hydrogen:
  (i) esterification—incorporating the R¹ group;
and then in all cases:
  (ii) acetylation and aromatisation—creating the core benzene ring and incorporating the acetyl group;
and subsequently:
  (iv) deprotection (de-esterification)—removing the R¹ group.

In one embodiment there is provided a compound of formula (II) of formula (IId):

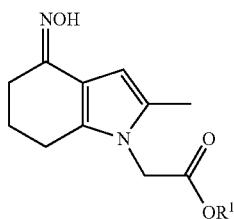

(IId)

wherein R¹ is selected from hydrogen, optionally substituted hydrocarbyl and optionally substituted heterocyclyl; or a salt thereof.

In one embodiment there is provided the use of a compound of formula (II) of formula (IId), or a salt thereof, as defined herein, as a pharmaceutical intermediate.

In one embodiment there is provided the use of a compound of formula (II) of formula (IId), or a salt thereof, as defined herein, as an intermediate for the manufacture of the compound of formula (I), or a salt thereof.

The compound of formula (IId) may be prepared by reacting a compound of formula (IIa) with hydroxylamine or a salt thereof, for example hydroxylamine hydrochloride.

The compound of formula (IId) may be converted into the compound of formula (I) by carrying out the following transformations:
when R¹ is hydrogen:
  (i) esterification—incorporating the R¹ group;
and then in all cases:
  (ii) thioarylation—incorporating the thioaryl group;
  (iii) acetylation and aromatisation—creating the core benzene ring and incorporating the acetyl group;
and subsequently:
  (iv) deprotection (de-esterification)—removing the R¹ group;
wherein steps (ii) and (iii) may be performed in either order.

In another aspect, there is provided a compound of the formula (XI):

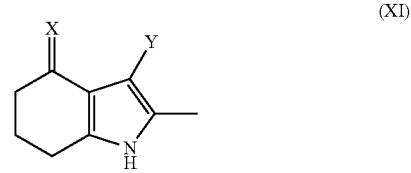

(XI)

wherein:
X is =O, =N—OH or =N—OC(O)Me;
Y is

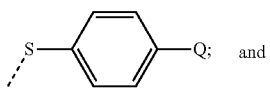

and

Q is hydrogen or chloro;
or a salt thereof.

A compound of the formula (XI) may be used to prepare a compound of the formula (I), using, for example, the route described in Scheme VI below.

In one embodiment, there is provided a compound of formula (XIa):

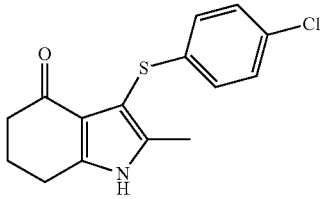

(XIa)

A compound of the formula (XIa) may be prepared from a compound of formula (XII):

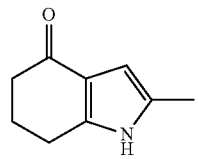

(XII)

using similar methods to those described in the preparation of a compound of the formula (IIb) from a compound of the formula (IIa) and (IVa) or (IVb).

In another embodiment, there is provided a compound of formula (XIb):

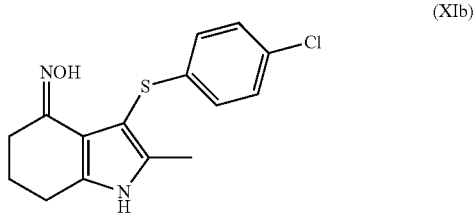

A compound of formula (XIb) may be prepared from a compound of formula (XIa), using similar methods to those described for the preparation of a compound of formula (IIc) from (IIb).

In one embodiment a "hydrocarbyl" is a radical consisting of hydrogen atoms and from 1 to 15 carbon atoms, wherein the hydrocarbyl may be saturated, partially saturated or fully unsaturated, and may contain linear, branched or cyclic elements.

In one embodiment a "heterocyclyl" is a 4-12 membered monocyclic or bicyclic ring system, wherein the heterocyclyl contains 1-4 heteroatoms each selected from N, S and O, wherein the heterocyclyl may be fully saturated, partially saturated or fully unsaturated.

Those skilled in the art will appreciate that certain compounds of the invention can exist as isomers, for example compounds of formula (II). The invention encompasses all isomeric forms of compounds depicted herein and mixtures thereof unless indicated otherwise.

In this specification, the term "alkyl" includes both straight and branched chain alkyl groups.

References to individual alkyl groups such as "propyl" are specific for the straight chain version only, and references to individual branched chain alkyl groups such as "isopropyl" are specific for the branched chain version only. This convention applies to other radicals described within this specification such as alkenyl radicals, alkynyl radicals, alkoxy radicals and alkanoyl radicals.

For example, "$C_{1-6}$alkyl" includes $C_{1-4}$alkyl, $C_{1-3}$alkyl, methyl, ethyl, propyl, isopropyl and t-butyl.

In this specification "$C_{2-6}$alkenyl" includes $C_{2-3}$alkenyl, butenyl, isobutenyl, 1,5-hexadien-3-yl.

Examples of the term "$C_{2-6}$alkynyl" include $C_{2-3}$alkynyl, butynyl, propynyl and ethynyl.

Examples of the term "$C_{1-6}$alkoxy" include $C_{1-3}$alkoxy, t-butyloxy, isopropoxy, butoxy, ethoxy and methoxy.

Examples of the term "($C_{1-6}$alkyl)-S(O)$_a$— wherein a is 0 to 2" include "($C_{1-6}$alkyl)-S—", "($C_{1-3}$alkyl)-S(O)$_a$— wherein a is 0 to 2", "($C_{1-3}$alkyl)-S(O)$_2$—", isopropylsulfanyl, propylsulfonyl, mesyl and ethylsulfanyl, butanesulfinyl and isopentylsulfinyl.

Examples of the term "$C_{1-6}$alkoxycarbonyl" include $C_{1-3}$alkoxycarbonyl, methoxycarbonyl, ethoxycarbonyl, isopropoxycarbonyl and isopentoxycarbonyl.

Examples of the term "$C_{1-6}$alkylsulfonyl" include $C_{1-3}$alkylsulfonyl, mesyl, ethylsulfonyl, isopropylsulfonyl and isobutylsulfonyl.

Examples of the term "$C_{1-6}$ alkanoyl" include $C_{1-3}$alkanoyl, formyl, acetyl and propionyl.

Examples of the term "N—($C_{1-6}$alkyl)amino" include N—($C_{1-3}$alkyl)amino, methylamino, isopropylamino and isohexylamino.

Examples of the term "N,N—($C_{1-6}$alkyl)$_2$-amino" include N,N—($C_{1-3}$alkyl)$_2$-amino, N,N-dimethylamino, N-isopropyl-N-methylamino and N-pentyl-N-ethylamino.

Examples of the term "N—($C_{1-6}$alkanoyl)-N—($C_{1-6}$alkyl) amino" include N—($C_{1-3}$alkanoyl)-N—($C_{1-6}$alkyl)amino, N-propionoyl-N—($C_{1-6}$alkyl)amino, N-propionoylamino, N-acetyl-N-methylamino and N-acetyl-N-cyclopropylamino.

Examples of "N—($C_{1-6}$alkyl)carbamoyl" include N—($C_{1-3}$alkyl)carbamoyl, N-isopentylaminocarbonyl, N-methylaminocarbonyl and N-ethylaminocarbonyl.

Examples of "N,N—($C_{1-6}$alkyl)$_2$-carbamoyl" include N,N—($C_{1-3}$alkyl)$_2$-carbamoyl, N-isopentyl-N-ethylaminocarbonyl, N,N-dimethylaminocarbonyl and N-methyl-N-ethylaminocarbonyl.

Examples of "N—($C_{1-6}$alkyl)sulfamoyl" include N—($C_{1-3}$alkyl)sulfamoyl, N-isopentylsulfamoyl, N-methylsulfamoyl and N-ethylsulfamoyl.

Examples of "N,N—($C_{1-6}$alkyl)$_2$sulfamoyl" include N,N—($C_{1-3}$alkyl)$_2$sulfamoyl, N-isopentyl-N-ethylsulfamoyl, N,N-dimethylsulfamoyl and N-methyl-N-ethylsulfamoyl.

A salt formed from a compound of the invention where $R^1$ is hydrogen may be an alkali metal salt, for example a sodium or potassium salt, an alkaline earth metal salt, for example a calcium or magnesium salt, an ammonium salt or a salt with an organic base, for example a salt with methylamine, dimethylamine, trimethylamine, piperidine, morpholine or triethanolamine.

A salt of a compound of the invention where $R^1$ contains a basic group, is for example, an acid-addition salt with, for example, an inorganic or organic acid, for example hydrochloric, hydrobromic, sulphuric, phosphoric, trifluoroacetic, citric or maleic acid.

A salt of a compound of the invention where $R^1$ contains an acidic group, is for example an alkali metal salt, for example a sodium or potassium salt, an alkaline earth metal salt, for example a calcium or magnesium salt, an ammonium salt or a salt with an organic base, for example a salt with methylamine, dimethylamine, trimethylamine, piperidine, morpholine or triethanolamine.

In one embodiment $R^1$ is hydrogen or an optionally substituted hydrocarbyl.

In one embodiment the optional substituents on a "hydrocarbyl" and "heterocyclyl" are selected from halo, nitro, cyano, hydroxy, $C_{1-6}$alkyl, $C_{1-6}$alkoxy, $C_{1-6}$alkanoyl, N—($C_{1-6}$alkyl)amino, N,N—($C_{1-6}$alkyl), amino, N—($C_{1-6}$alkanoyl)amino, $C_{1-6}$alkoxycarbonyl, N—($C_{1-6}$alkanoyl)-N—($C_{1-6}$alkyl)amino, carbamoyl, sulfamoyl, N—($C_{1-6}$alkyl)carbamoyl, N,N—($C_{1-6}$alkyl)$_2$-carbamoyl, N—($C_{1-6}$alkyl)sulfamoyl, N,N—(C sulfamoyl and ($C_{1-6}$alkyl)-S(O)$_a$— wherein a is 0-2.

In a further embodiment $R^1$ is hydrogen or an unsubstituted hydrocarbyl.

In a further embodiment $R^1$ is hydrogen.

In a further embodiment $R^1$ is an optionally substituted hydrocarbyl.

In a further embodiment $R^1$ is an unsubstituted hydrocarbyl.

In a further embodiment $R^1$ is selected from hydrogen, $C_{1-6}$alkyl, $C_{2-6}$alkenyl, $C_{2-6}$alkynyl, $C_{3-6}$cycloalkyl, optionally substituted phenyl and optionally substituted benzyl;

In a further embodiment $R^1$ is selected from hydrogen, $C_{1-6}$alkyl, $C_{2-6}$alkenyl, $C_{2-6}$alkynyl, $C_{3-6}$cycloalkyl, phenyl and benzyl; wherein the phenyl and benzyl are optionally substituted by one or more halo, nitro, cyano, hydroxy, $C_{1-6}$alkyl, $C_{1-6}$alkoxy, $C_{1-6}$alkanoyl, N—($C_{1-6}$alkyl)amino, N,N—($C_{1-6}$alkyl)$_2$-amino, N—($C_{1-6}$alkanoyl)amino, N—($C_{1-6}$alkanoyl)-N—($C_{1-6}$alkyl)amino, carbamoyl, sulfamoyl, N—($C_{1-6}$alkyl)carbamoyl, N,N—($C_{1-6}$alkyl)$_2$-carbamoyl, N—($C_{1-6}$alkyl)sulfamoyl, N,N—($C_{1-6}$alkyl)$_2$sulfamoyl or ($C_{1-6}$alkyl)-S(O)$_a$— wherein a is 0-2.

In a further embodiment $R^1$ is selected from $C_{1-6}$alkyl, $C_{2-6}$alkenyl, $C_{2-6}$alkynyl, $C_{3-6}$cycloalkyl, phenyl and benzyl; wherein the phenyl and benzyl are optionally substituted by one or more halo, nitro, cyano, hydroxy, $C_{1-6}$alkyl, $C_{1-6}$alkoxy, $C_{1-6}$alkanoyl, N—($C_{1-6}$alkyl)amino, N,N—($C_{1-6}$alkyl)$_2$-amino, N—($C_{1-6}$alkanoyl)amino, N—($C_{1-6}$alkanoyl)-N—($C_{1-6}$alkyl)amino, carbamoyl, sulfamoyl, N—($C_{1-6}$alkyl)carbamoyl, N,N—($C_{1-6}$alkyl)$_2$-carbamoyl, N—($C_{1-6}$alkyl)sulfamoyl, N,N—($C_{1-6}$alkyl)$_2$sulfamoyl or ($C_{1-6}$alkyl)-S(O)$_a$— wherein a is 0-2.

In a further embodiment $R^1$ is selected from hydrogen, $C_{1-6}$alkyl, $C_{2-6}$alkenyl, $C_{2-6}$alkynyl, $C_{3-6}$cycloalkyl, phenyl and benzyl.

In a further embodiment $R^1$ is selected from $C_{1-6}$alkyl, $C_{2-6}$alkenyl, $C_{2-6}$alkynyl, $C_{3-6}$cycloalkyl, phenyl and benzyl.

In a further embodiment $R^1$ is selected from hydrogen and $C_{1-6}$alkyl.

In a further embodiment $R^1$ is selected from hydrogen and ethyl.

In a further embodiment $R^1$ is $C_{1-6}$alkyl.

In a further embodiment $R^1$ is ethyl.

In a further embodiment Q is chloro.

In a further embodiment X is =O or =N—OH.

In a further embodiment X is =N—OC(O)Me.

In a further embodiment X is =O.

In a further embodiment X is =N—OH.

Therefore, in one embodiment there is provided a compound of formula (II), as depicted hereinabove, wherein:

$R^1$ is selected from hydrogen, $C_{1-6}$alkyl, $C_{2-6}$alkenyl, $C_{2-6}$alkynyl, $C_{3-6}$cycloalkyl, phenyl and benzyl; wherein the phenyl and benzyl are optionally substituted by one or more halo, nitro, cyano, hydroxy, $C_{1-6}$alkyl, $C_{1-6}$alkoxy, $C_{1-6}$alkanoyl, N—($C_{1-6}$alkyl)amino, N,N—($C_{1-6}$alkyl)$_2$-amino, N—($C_{1-6}$alkanoyl)amino, N—($C_{1-6}$alkanoyl)-N—($C_{1-6}$alkyl)amino, carbamoyl, sulfamoyl, N—($C_{1-6}$alkyl)carbamoyl, N,N—($C_{1-6}$alkyl)$_2$-carbamoyl, N—($C_{1-6}$-alkyl)sulfamoyl, N,N—($C_{1-6}$alkyl)$_2$sulfamoyl or ($C_{1-6}$alkyl)-S(O)$_a$— wherein a is 0-2;

X is =O or =N—OH;

Y is hydrogen or

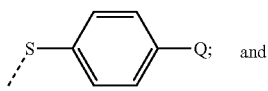
Q; and

Q is hydrogen or chloro;
or a salt thereof.

In a further embodiment there is provided a compound of formula (II), as depicted hereinabove, wherein:

$R^1$ is selected from $C_{1-6}$alkyl, $C_{2-6}$alkenyl, $C_{2-6}$alkynyl, $C_{3-6}$cycloalkyl, phenyl and benzyl; wherein the phenyl and benzyl are optionally substituted by one or more halo, nitro, cyano, hydroxy, $C_{1-6}$alkyl, $C_{1-6}$alkoxy, $C_{1-6}$alkanoyl, N—($C_{1-6}$alkyl)amino, N,N—($C_{1-6}$alkyl)$_2$-amino, N—($C_{1-6}$alkanoyl)amino, N—($C_{1-6}$alkanoyl)-N—($C_{1-6}$alkyl)amino, carbamoyl, sulfamoyl, N—($C_{1-6}$alkyl)carbamoyl, N,N—($C_{1-6}$alkyl)$_2$-carbamoyl, N—($C_{1-6}$alkyl)sulfamoyl, N,N—($C_{1-6}$alkyl)$_2$-sulfamoyl or ($C_{1-6}$alkyl)-S(O)$_a$— wherein a is 0-2;

X is =O or =N—OH;

Y is hydrogen or

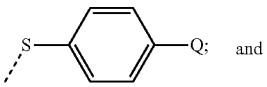
Q; and

Q is hydrogen or chloro;
or a salt thereof.

In a further embodiment there is provided the use of a compound of formula (II), as depicted hereinabove, wherein:

$R^1$ is selected from $C_{1-6}$alkyl, $C_{2-6}$alkenyl, $C_{2-6}$alkynyl, $C_{3-6}$cycloalkyl, phenyl and benzyl; wherein the phenyl and benzyl are optionally substituted by one or more halo, nitro, cyano, hydroxy, $C_{1-6}$alkyl, $C_{1-6}$alkoxy, $C_{1-6}$alkanoyl, N—($C_{1-6}$alkyl)amino, N,N—($C_{1-6}$alkyl)$_2$-amino, N—($C_{1-6}$alkanoyl)amino, N—($C_{1-6}$alkanoyl)-N—($C_{1-6}$alkyl)amino, carbamoyl, sulfamoyl, N—($C_{1-6}$alkyl)carbamoyl, N,N—($C_{1-6}$alkyl)$_2$-carbamoyl, N—($C_{1-6}$alkyl)sulfamoyl, N,N—($C_{1-6}$alkyl)$_2$sulfamoyl or ($C_{1-6}$alkyl)-S(O)$_a$— wherein a is 0-2;

X is =O or =N—OH;

Y is hydrogen or

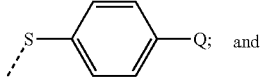
Q; and and

Q is hydrogen or chloro;
or a salt thereof;
as a pharmaceutical intermediate.

In a further embodiment there is provided the use of a compound of formula (II), as depicted hereinabove, wherein:

$R^1$ is selected from $C_{1-6}$alkyl, $C_{2-6}$alkenyl, $C_{2-6}$alkynyl, $C_{3-6}$cycloalkyl, phenyl and benzyl; wherein the phenyl and benzyl are optionally substituted by one or more halo, nitro, cyano, hydroxy, $C_{1-6}$alkyl, $C_{1-6}$alkoxy, $C_{1-6}$alkanoyl, N—($C_{1-6}$alkyl)amino, N,N—($C_{1-6}$alkyl)$_2$-amino, N—($C_{1-6}$alkanoyl)amino, N—($C_{1-6}$alkanoyl)-N—($C_{1-6}$alkyl)amino, carbamoyl, sulfamoyl, N—($C_{1-6}$alkyl)carbamoyl, N,N—($C_{1-6}$alkyl)$_2$-carbamoyl, N—($C_{1-6}$alkyl)sulfamoyl, N,N—($C_{1-6}$alkyl)$_2$sulfamoyl or ($C_{1-6}$alkyl)-S(O)$_a$— wherein a is 0-2;

X is =O or =N—OH;

Y is hydrogen or

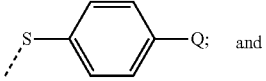
Q; and

Q is hydrogen or chloro;
or a salt thereof;
as an intermediate for the preparation of the compound of formula (I), or a salt thereof.

In a further embodiment there is provided a compound of formula (II), as depicted hereinabove, wherein:

$R^1$ is selected from $C_{1-6}$alkyl, $C_{2-6}$alkenyl, $C_{2-6}$alkynyl, $C_{3-6}$cycloalkyl, phenyl and benzyl;

X is =O or =N—OH;

Y is hydrogen or 4-chlorophenylsulfanyl;

or a salt thereof.

In a further embodiment there is provided the use of a compound of formula (II), as depicted hereinabove, wherein:

$R^1$ is selected from $C_{1-6}$alkyl, $C_{2-6}$alkenyl, $C_{2-6}$alkynyl, $C_{3-6}$cycloalkyl, phenyl and benzyl;

X is =O or =N—OH;

Y is hydrogen or 4-chlorophenylsulfanyl;

or a salt thereof, as a pharmaceutical intermediate.

In a further embodiment there is provided the use of a compound of formula (II), as depicted hereinabove, wherein:

$R^1$ is selected from $C_{1-6}$alkyl, $C_{2-6}$alkenyl, $C_{2-6}$alkynyl, $C_{3-6}$cycloalkyl, phenyl and benzyl;

X is =O or =N—OH;

Y is hydrogen or 4-chlorophenylsulfanyl;

or a salt thereof;

as an intermediate for the manufacture of the compound of formula (I), or a salt thereof.

In a further embodiment there is provided a compound of formula (II), as depicted hereinabove, wherein:

$R^1$ is selected from $C_{1-6}$alkyl;

X is =O or =N—OH;

Y is hydrogen or 4-chlorophenylsulfanyl;

or a salt thereof.

In a further embodiment there is provided the use of a compound of formula (II), as depicted hereinabove, wherein:

$R^1$ is selected from $C_{1-6}$alkyl;

X is =O or =N—OH;

Y is hydrogen or 4-chlorophenylsulfanyl;

or a salt thereof;

as a pharmaceutical intermediate.

In a further embodiment there is provided the use of a compound of formula (II), as depicted hereinabove, wherein:

$R^1$ is selected from $C_{1-6}$alkyl;

X is =O or =N—OH;

Y is hydrogen or 4-chlorophenylsulfanyl;

or a salt thereof;

as an intermediate for the manufacture of the compound of formula (I), or a salt thereof.

A further aspect of the invention provides a process for the preparation of the pharmaceutical compound of formula (I), or a salt or ester thereof, comprising reaction of a compound of formula (IIc), as depicted hereinbefore, with an acetylating agent;

wherein the values of $R^1$ is as defined hereinabove and wherein Q is chloro;

and thereafter, optionally reacting with acid or base.

The reaction with an acid or base achieves hydrolysis of the ester group (when $R^1$ is other than hydrogen) to provide the compound of formula (I) or a salt thereof.

The intermediate product mixture may contain predominantly the desired amide of formula (V) or it may comprise a mixture of the amide of formula (V) and the imide of formula (VI) as shown in Scheme (II):

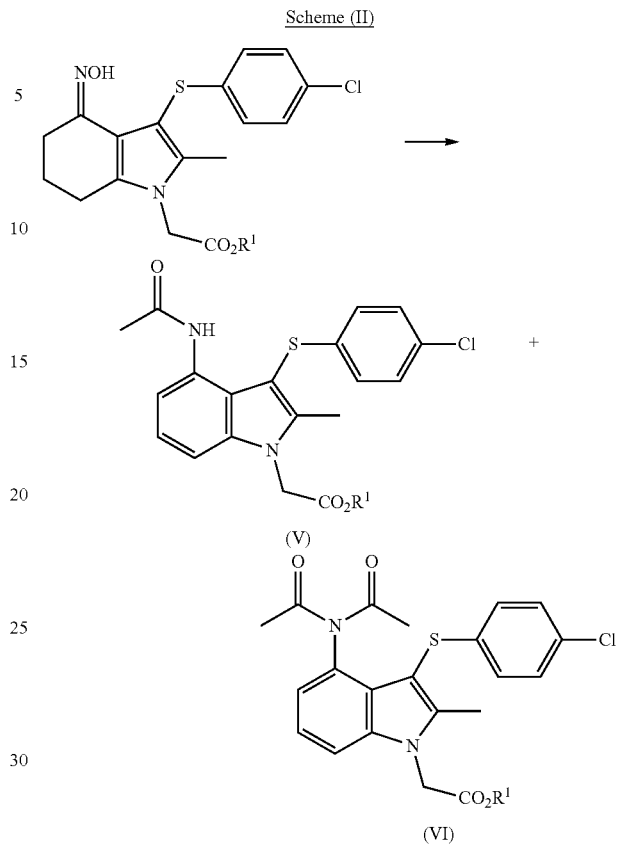

Scheme (II)

The mixture of amide (V) and imide (VI) may be converted to predominantly amide (V) by treatment with aqueous acid in the presence of an organic co-solvent, for example ethanol. Alternatively the mixture may be subjected to de-esterification (hydrolysis) conditions under which the imide group is converted to the amide, and the product isolated is the compound of formula (I) or a salt thereof. Amide (V) may optionally be recrystallised from a solvent such as ethanol to increase purity prior to de-esterification.

In one embodiment there is provided a process comprising reaction of a compound of formula (II) of formula (IIc), as depicted hereinbefore, with an acetylating agent; wherein the values of $R^1$ are as defined in claims 1 to 8, and wherein Q is chloro.

Therefore in one embodiment there is provided a process for the preparation of the pharmaceutical compound of formula (I), or a salt thereof, comprising reaction of a compound of formula (IIc), as depicted hereinbefore, with an acetylating agent;

wherein the values of $R^1$ is as defined hereinabove and wherein Q is chloro;

and thereafter de-esterifying to provide the compound of formula (I), or a salt thereof.

The process to de-esterify may involve reaction with a base or with an acid or with hydrogen in the presence of a catalyst.

In one embodiment the process to de-esterify may involve reaction with a base.

Surprisingly it has been found that certain reaction conditions advantageously disfavour the formation of imide. For example, by reducing the amount of acetic anhydride to 4 molar eq. and using sodium iodide at 85° C. in order to keep the reaction time around 4.5 h.

Examples of suitable bases are inorganic bases, for example metal hydroxides, for example LiOH, NaOH or KOH.

As discussed hereinabove, the compound of formula (IId) has been found to be surprisingly useful as an intermediate for the preparation of pharmaceutical compound (I) or salts thereof. In a further aspect of the invention there is provided a process comprising the reaction of a compound of formula (IId) as depicted hereinbefore, with an acetylating agent, wherein $R^1$ is as defined herein.

The products of this reaction are amide (VI) and imide (VII):

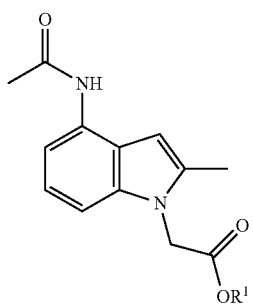

(VI)

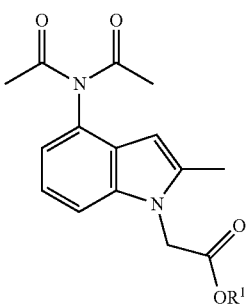

(VII)

These products may be carried forward as a mixture to the next stage and the hydrolysis conditions used later in the synthesis causes conversion of imide to desired amide to deliver the compound of formula (I) or a salt thereof.

The acetylation processes involving the compound of formula (IIc) and (IId) may be carried out in a solvent such as an aromatic hydrocarbon solvent, for example toluene, xylene or mesitylene, or a ketone solvent, for example methylisobutylketone (MIBK), methylethylketone (MEK), carboxylic acid solvents, for example acetic acid, or ether solvents, for example 2-methyltetrahydrofuran.

The acetylation process involving the compound of formula (IIc) and (IId) works best at an elevated temperature, for example up to around 140° C.

A further aspect of the present invention provides an improved process wherein the reaction of a compound of formula (IIc) or (IId) with an acetylating agent is carried out in the presence of an iodide salt.

Surprisingly, the presence of an iodide salt in the reaction has been found to allow a reduction in the temperature required for the reaction to proceed efficiently. Examples of iodide salts are metal iodides, for example KI, NaI, LiI, and ammonium iodide salts, for example $(C_{1-6}alkyl)_4NI$, for example tetra-N-butylammonium iodide. The reaction temperature required for these processes can be reduced to 80-100° C. from the usual much higher temperatures by inclusion of an iodide salt in the reaction mixture. A substoichiometric quantity of iodide salt is sufficient to provide the beneficial effect.

Other conditions have been invented that allow efficient reaction at an advantageously reduced temperature without the presence of an iodide salt. Surprisingly the use of a carboxylic acid as a co-solvent in the reaction results in an efficient reaction at an advantageously reduced temperature.

Therefore, a further aspect of the invention provides an improved process wherein the reaction of a compound of formula (IIc) or (IId) with an acetylating agent is carried out in the presence of a carboxylic acid co-solvent.

Suitable carboxylic acids co-solvents may be carboxylic acids containing from 1 to 7 carbon atoms, for example acetic acid.

For example, use of a 50:50 mixture of xylene or mesitylene and acetic acid allows the reaction to proceed in the absence of an iodide catalyst at a temperature of 105-110° C. whereas in the same solvent mixture in the presence of 5 mol % of either sodium iodide or tetrabutylammonium iodide, the reaction proceeds at the lower temperature of 95-100° C.

A further aspect of the present invention provides an improved process wherein the acetylation process involving compound (IIc) or (IId) is carried out in the presence of a Lewis acid. One example of a Lewis acid is $FeCl_3$. Surprisingly the presence of a Lewis acid has been found to allow the acetylation reaction to proceed efficiently at much lower temperature than is otherwise required. The presence of $FeCl_3$ allows the reaction to proceed at a temperature as low as 70° C.

Acetylating agents are well known to the skilled person. Acetylating agents that may be used for the acetylation process involving the compound of formula (IIc) and (IId) include acetic anhydride, acetyl halides such as acetyl chloride, and thioesters such as phenyl thioacetate. Phenyl thioacetate was found to give better conversion than with acetic anhydride alone under comparable conditions. Alternatively the process may make use of other acylating agents, for example benzoic anhydride or pivalic anhydride. The amide groups in the products of such reactions would then need to be hydrolysed and the resulting amines then acetylated using an acetylation agent.

In a still further embodiment the invention provides a process for the preparation of a compound of formula (I):

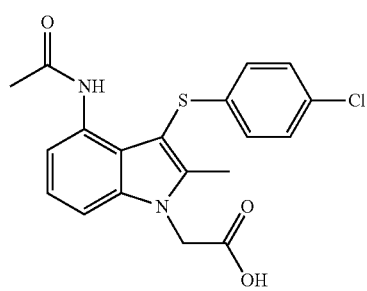

(I)

which comprises reaction of a compound of formula (IIAA):

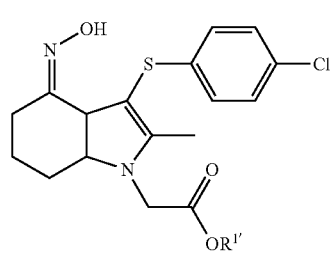

(IIAA)

where $R^{1'}$ is hydrogen or $C_{1-6}alkyl$ with an acylating agent followed by de-esterification.

In one embodiment R[1'] is hydrogen or ethyl.

In one embodiment the acylating agent is $Ac_2O$.

In one embodiment the process is carried out in the presence of xylene and sodium iodide.

In a still further embodiment the invention provides a compound of formula (I) prepared according to a process as defined in any one of claims 11 to 20.

The various aspects of the invention are illustrated by the following Examples. Three routes are illustrated in Schemes (III), (IV), (V) and (VI), below.

ABBREVIATIONS AND GENERAL PROCEDURES

The analytical techniques used include gas chromatography (GC), high performance liquid chromatography (HPLC), liquid chromatography-mass spectrometry (LC-MS) and ultra-high performance liquid chromatography-mass spectroscopy (UHPLC-MS). Mass spectrometry data (m/z) is provided together with an assignment of the peak(s) observed. Nuclear magnetic resonance (NMR) data was obtained at 300 MHz, 400 Mz or 500 Mhz in $d_6$-dimethylsulfoxide unless otherwise specified. Standard abbreviations are used (s=singlet, d=doublet, m=multiplet, dd=doublet of doublets, t=triplet, q=quartet, br=broad). Solvents used include ethanol (EtOH), methanol (MeOH), tetrahydrofuran (THF), ethyl acetate (EtOAc), methylisobutylketone (MIBK), methyl tert-butyl ether (MTBE) and acetic acid (AcOH). Generally, reactions were carried out under an atmosphere of nitrogen. Unless otherwise stated, procedures were carried out at ambient temperature (room temperature, r.t.), with stirring, for a number of hours (h) or minutes (mins). Mole equiv represents the molar equivalents of the reagent relative to the specified limiting reagent. Rel vol (relative volume) represents the amount of solvent relative to a unit mass of the specified limiting reagent e.g. L/kg. Rel wt (relative weight) represents the amount of a material by weight relative to a unit weight of the specified limiting reagent e.g. kg/kg. Assays by HPLC, GC and NMR were performed against fully characterised reference standards using standard procedures that are well known in the art. TCCA=trichloroisocyanuric acid. GC analysis can be performed on a DB-1 column (30 m×0.25 mm id, 0.25 μm) using nitrogen as carrier gas using an appropriate temperature gradient and flame ionisation detection. HPLC analysis can be performed on either a Waters Symmetry C18 column (150 mm×3.0 mm, 3.5 μm) or Zorbax SB-C8 column (150 mm×3.0 mm, 3.5 μm) or Hichrom Ace Phenyl column (50 mm×3.0 mm, 3 μm) eluting with an appropriate aqueous acetonitrile gradient buffered with TFA and UV detection (230 or 250 nm). UHPLC was performed on either a BEH C18 column (100 mm×2.1 mm, 1.7 μm) or BEH Phenyl (100 mm×2.1 mm, 1.7 μm) eluting with an appropriate aqueous acetonitrile gradient buffered with TFA or ammonium acetate respectively with UV detection (250 nm). UHPLC-MS can be done using +ve or −ve electrospray ionisation at a capillary voltage of 3.5 kV and a cone voltage increasing from 10 to 60V. LC-MS can be performed on a Hichrom Ace Phenyl column (50 mm×3.0 mm, 3 μm) eluting with an appropriate aqueous acetonitrile gradient buffered with TFA and UV detection (230 nm) using combined APCI/+ve electrospray ionisation.

Scheme (III)

Route 1

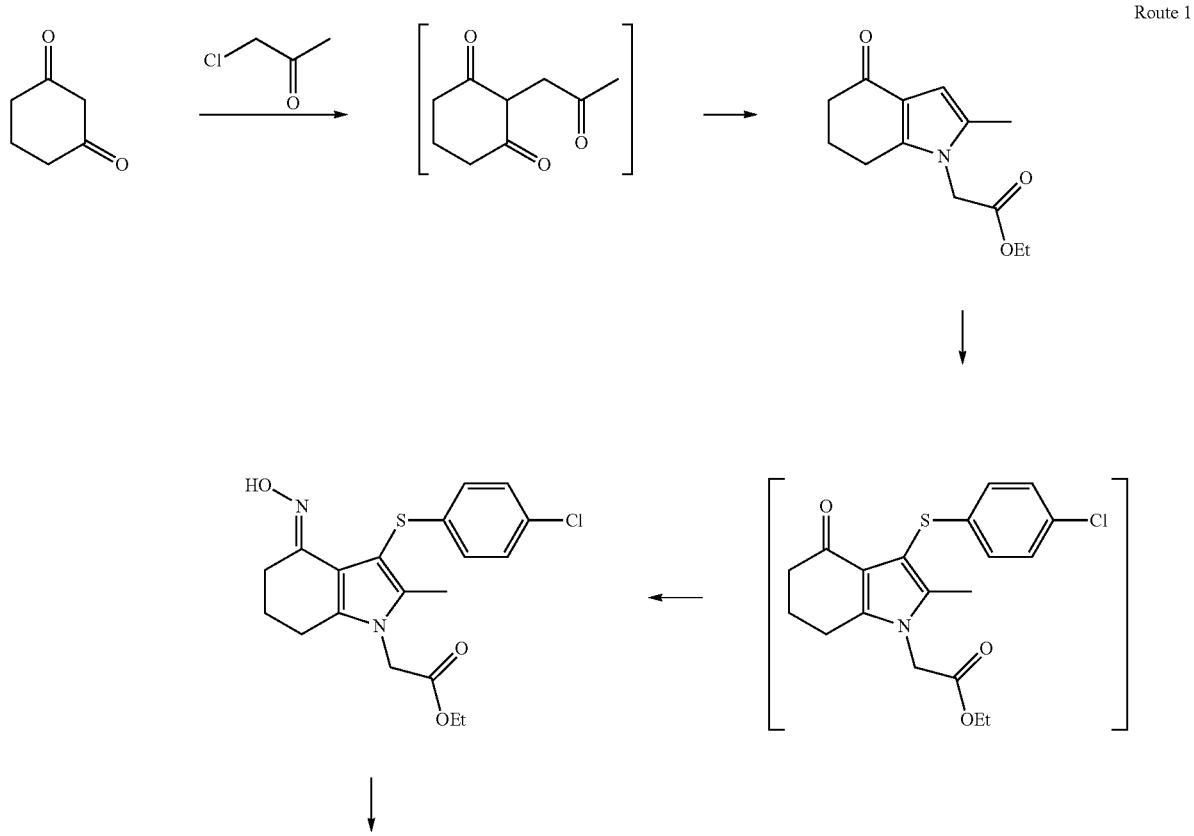

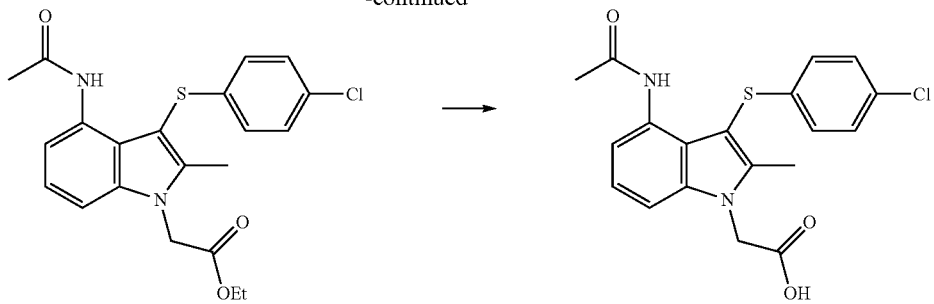

-continued

Ethyl(2-methyl-4-oxo-4,5,6,7-tetrahydro-1H-indol-1-yl)acetate

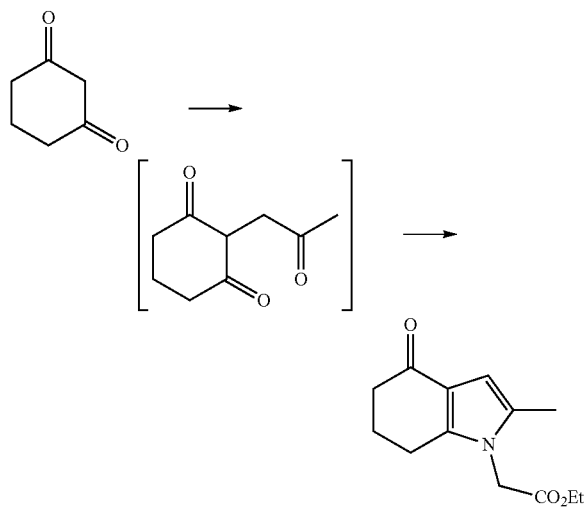

A solution of KOH (2.54 kg, 2.26 kg corrected for assay, 40.2 moles) in water (4.0 L) was added over 30 mins to a solution of cyclohexane-1,3-dione (4.53 kg, 4.51 kg corrected for assay, 40.2 moles) in EtOH (16.2 L), while maintaining the temperature below 30° C. After stirring for 15 mins at r.t., freshly distilled chloroacetone (4.39 kg, 3.83 kg corrected for assay, 41.4 mol) was then added slowly to the mixture, maintaining a temperature of 25-28° C. The resulting slurry was stirred at r.t. for 19 h. Inorganic by-products were then removed by filtration and were washed on the filter with EtOH (4.5 L). The filtrates were combined to provide 2-(2-oxopropyl)cyclo-hexane-1,3-dione as a solution in EtOH. Assay by GC 26.5% w/w; purity by GC: 82.3 area %). This solution was transferred to a reactor and glycine ethyl ester hydrochloride salt (6.41 kg, 6.17 kg corrected for assay, 44.2 moles) was added at r.t. with stirring followed by sodium acetate trihydrate (6.04 kg, 6.02 kg corrected for assay, 44.3 moles). The mixture was diluted with ethanol (28.9 L) then heated under reflux for 2 h. EtOH was removed in vacuo (−0.850 to −0.900 bar) at 30° C. until 40 L of distillate had been collected. After cooling the residue to 0° C., water (15 L) was added, while maintaining a temperature of 0-5° C. After stirring for a further 1 h at this temperature, the solid that separated out was collected by filtration and was then dried in vacuo at 35° C. with a nitrogen bleed to give the title compound as a solid; 6.7 kg; assay by $^1$H NMR: 86.6% w/w; weight corrected for assay: 5.80 kg (61% over 2 steps); purity by GC: 96.0 area %; m/z: 235 (MH$^+$); $^1$H NMR: (CDCl$_3$) 1.27-1.32 (3H, t), 2.10-2.17 (2H, m), 2.19 (3H, s), 2.42-2.46 (2H, t), 2.65-2.69 (2H, t), 4.21-4.28 (2H, m), 4.51 (2H, s) and 6.27 (1H, s).

Alternative Procedures for Synthesising the ethyl(2-methyl-4-oxo-4,5,6,7-tetrahydro-1H-indol-1-yl)acetate

Alternative Procedure 1

A solution of potassium hydroxide (23.58 g, 20.0 g corrected for assay, 357 mmol) in water (36 mL) at r.t. was added to a solution of 1,3-cyclohexanedione (39.97 g, 356 mmol) in ethanol (144 mL) with stirring (exothermic addition). After stirring for 15 mins at 20° C., redistilled chloroacetone (37.62 g, 33.9 g corrected for assay, 366 mmol) was added in one portion and the reaction mixture stirred for 20 h at 20° C. The inorganic by products were removed by filtration, washing the filter cake with ethanol (40 mL) and the filtrates were combined to provide 2-(2-oxo-propyl)cyclohexane-1,3-dione as a solution in aqueous ethanol. To this solution were added glycine ethyl ester hydrochloride (54.73 g, 392 mmol) and anhydrous sodium acetate (32.19 g, 392 mmol). The reaction mixture was heated to reflux (75° C. internal temperature) for 1 h then cooled to 20° C. and stirred for 19 h. The mixture was heated to reflux (internal temperature 75° C.) and water (116 mL) added, then cooled to 20° C. over 30 mins. A small amount of 2-methyl-4-oxo-4,5,6,7-tetrahydro-1H-indol-1-yl)-acetic acid, ethyl ester was added as a seed (10 mg) and, after a few minutes, crystallization of the product was observed. The slurry was stirred for 30 mins, then cooled to 5° C. and stirred for 18 h. The solid was collected by filtration, washed with water (2×80 mL) followed by tert-butyl methyl ether (2×80 mL) and then dried in vacuo at 40° C. for 20 h to provide ethyl(2-methyl-4-oxo-4,5,6,7-tetrahydro-1H-indol-1-yl)acetate as a pale yellow crystalline solid, 41.77 g (49.8% yield). MP 105.1 to 105.4° C. Assay by $^1$H-NMR 99.3% w/w. Purity by GC 100 area %.

Alternative Procedure 2

In reaction vessel 1, potassium hydroxide (11.78 g, 10.0 g corrected for assay, 178 mmol)) was dissolved in water (72 mL) with stirring (highly exothermic) then the solution was cooled back to 20° C. 1,3-cyclohexanedione (20.0 g, 178 mmol) was added (exothermic addition) and the resulting dark red solution was stirred at 20° C. for 5 mins. Redistilled chloroacetone (18.9 g, 17.0 g corrected for assay, 184 mmol) was added in one portion, rinsing in with ethanol (18 mL) and the reaction mixture was stirred overnight at 20° C. The resulting solution of 2-(2-oxopropyl)cyclohexane-1,3-dione, volume 124 mL, was split into 4 equal portions. Glycine ethyl ester hydrochloride (6.85 g, 49.0 mmol), anhydrous sodium acetate (4.02 g, 49.0 mmol), water (26.5 mL) and ethanol (5.0 mL) were charged to reaction vessel 2 and stirring started. One portion of the solution of 2-(2-oxopropyl)cyclohexane-1,3-dione prepared above (31 mL) was then added to the contents of reaction vessel 2 with stirring and the resulting mixture was heated to 75° C., held at this temperature for 2 h, then cooled to 20° C. over 55 mins. After stirring overnight at 20° C., the solid was collected by filtration, washed with water (10 mL), tert-butyl methyl ether (2×10 mL) and then dried in vacuo 40° C. for 20 h to provide (2-methyl-4-oxo-4,5,6,7-tetrahydro-1H-indol-1-yl)-acetic acid ethyl ester as a beige solid, 5.88 g (56.0% yield). MP 101.2 to 103.5° C. Assay by $^1$H-NMR 95.3% w/w. Purity by GC 99.25 area %.

Alternative Procedure 3

A solution of potassium hydroxide (1.0 mole equiv) in water (0.9 rel vol) was added to a suspension of 1,3-cyclohexanedione (1.0 mole equiv, limiting reagent) in water (1.1 rel vol) with stirring over approximately 1 hour maintaining the temperature below 30° C. After a further 15 mins, chloroacetone (1.03 mole equiv) was added over approximately 4 hours then the reaction mixture was stirred overnight at 20° C. Glycine ethyl ester hydrochloride (1.1 mole equiv) and ethyl acetate (2 rel vol) were added followed by sodium acetate (1.1 mole equiv) and water (2 rel vol). The reaction mixture was heated at 60° C. for 2 h, then cooled to 50° C. where the aqueous phase was separated off and discarded. MTBE (4 rel vol) was added to the organic phase, the solution was warmed back up to 50° C. and then cooled to 35° C. over 20 mins. A seed of ethyl(2-methyl-4-oxo-4,5,6,7-tetrahydro-1H-indol-1-yl)acetate (0.0001 mole equiv) was added and the mixture cooled to 5° C. over 60 mins and aged overnight. The solid product was collected by filtration, washed with water (2 rel vol), followed by MTBE (2×2 rel vol) and then dried at 40° C. under vacuum to provide the title compound in 62% yield; purity 98% w/w.

Ethyl [3-(4-chloro-phenylsulfanyl)-4-(hydroxy-imino)-2-methyl-4,5,6,7-tetrahydro-1H-indol-1-yl]acetate

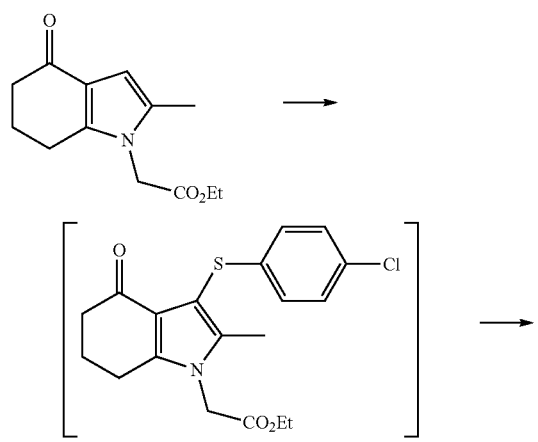

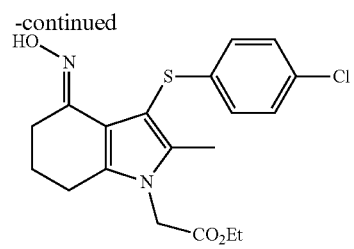

TCCA (1.16 kg, 5.01 moles) was added to a solution of bis-(4-chloro-phenyl)disulfide (4.83 kg, 4.80 kg corrected for assay, 16.7 moles) in EtOAc (56 L). The mixture was cooled to 0° C. and held at this temperature for 45 mins. Ethyl(2-methyl-4-oxo-4,5,6,7-tetrahydro-1H-indol-1-yl)acetate (6.48 kg, 5.61 kg corrected for assay, 23.9 moles) was then added in three portions (mildly exothermic). After stirring for 30 mins a sample was removed for analysis by HPLC then a solution of NaHCO$_3$ (1.12 kg, 13.3 moles) in water (22.5 L) was added. The mixture was warmed to r.t. over 30 mins and after stirring for a further 15 mins, a solid by-product was removed by filtration and washed with EtOAc (6.5 L). The filtrates were combined and the phases were allowed to separate. The aqueous layer was separated and extracted with EtOAc (11.2 L). The organic layers were combined and analysed which showed an assay by HPLC of 9.2% w/w and a purity by HPLC of 77.7 area %. The organic solution was then concentrated in vacuo until a volume of ~10-12 L remained (distillate volume ~60 L). EtOH (38.9 L) was added to the residue and distillation continued until ~35 L of distillate had been collected to leave the intermediate ethyl [3-(4-chlorophenylsulfanyl)-2-methyl-4-oxo-4,5,6,7-tetrahydro-1H-indol-1-yl]acetate as a solution in EtOH. Further EtOH (6.5 L) was added to this solution followed by hydroxylamine hydrochloride (2.15 kg, 30.9 moles) and anhydrous sodium acetate (2.60 kg, 2.55 kg corrected for assay, 31.1 moles) and the mixture was heated under reflux for 4 h. After cooling to r.t. over 1 h, the solid product was collected by filtration. The reactor was rinsed with 50% v/v ethanol:water (13 L) which was transferred to the filter. After drying briefly on the filter, the damp product was then transferred to a reactor and water (42 L) was added. The mixture was heated to 50° C. and stirred for 30 mins, then cooled back to r.t. The solid product was collected by filtration then charged back into the reactor damp and slurried in ethanol (19.4 L) at r.t for 30 mins. The solid was collected by filtration, washed with ethanol (9.7 L) followed by fresh ethanol (6.5 L) and then dried in vacuo at 40° C. to give the title compound as a solid; 7.00 kg; assay by $^1$H NMR 87.5% w/w; 6.1 kg corrected for assay (65% over 2 steps); purity by HPLC: 88.4 area %; m/z: 393 (MH$^+$); $^1$H NMR: 1.20-1.25 (3H, t), 1.79-1.86 (2H, m), 2.14 (3H, s), 2.50-2.51 (2H, t), 2.54-2.59 (2H, t), 4.15-4.22 (2H, m), 4.83 (2H, s), 6.92-6.95 (2H, d), 7.21-7.24 (2H, d) and 10.22 (1H, s). Data for an isolated sample of the intermediate ethyl [3-(4-chlorophenylsulfanyl)-2-methyl-4-oxo-4,5,6,7-tetrahydro-1H-indol-1-yl]acetate: $^1$H NMR: (CDCl$_3$) 1.33-1.37 (3H, t), 2.14-2.23 (2H, m), 2.27 (3H, s), 2.45-2.49 (2H, t), 2.74-2.78 (2H, t), 4.27-4.35 (2H, m), 4.64 (2H, s), 7.03-7.08 (2H, d) and 7.13-717 (2H, d).

Alternative Procedure for Synthesising the Intermediate ethyl [3-(4-chlorophenylsulfanyl)-2-methyl-4-oxo-4,5,6,7-tetrahydro-1H-indol-1-yl]acetate Bis-(4-chlorophenyl)disulfide (7.39 g, 25.7 mmol) was dissolved in EtOAc (86.5 mL) in reaction vessel 1 whilst cooling the mixture to 5° C. with stirring, resulting in a pale yellow solution. Sulfuryl chloride (2.1 mL, 25.7 mmol) was then added in a single portion (slightly exothermic) giving an orange-coloured solution after 15 mins. In a second reaction vessel, ethyl 2-(2-methyl-4-oxo-4,5,6,7-tetrahydro-1H-indol-1-yl)acetate (8.65 g, 36.8 mmol) was slurried in EtOAc (34.6 mL) with stirring whilst cooling the mixture to 5° C. The pre-cooled solution in reaction vessel 1 prepared above was added to the second vessel in 4 equal portions over 10 mins maintaining the temperature within the range 5-10° C., resulting in formation of a dark brown solution containing a small amount of insoluble material. The mixture was then allowed to warm to r.t. over 90 mins with stirring. A solution of sodium hydrogen carbonate (1.73 g, 20.6 mmol) in water (34.6 mL) was added and the resulting biphasic mixture was stirred for 15 mins. The layers were allowed to separate and the aqueous phase was discarded. The upper organic phase was dried over magnesium sulfate, which was subsequently removed by filtration to provide a solution of ethyl 2-(2-methyl-4-oxo-4,5,6,7-tetrahydro-1H-indol-1-yl)acetate in ethyl acetate, weight 132.6 g. Assay by HPLC 8.4% w/w, therefore 11.1 g ethyl 2-(2-methyl-4-oxo-4,5,6,7-tetrahydro-1H-indol-1-yl)acetate present (80%) yield.

Alternative Procedures for the Synthesis of ethyl [3-(4-chlorophenylsulfanyl)-4-(hydroxyimino)-2-methyl-4,5,6,7-tetrahydro-1H-indol-1-yl]acetate Alternative Procedure 1

In vessel 1, bis-(4-chlorobenzene)disulfide (0.53 mole equiv) was suspended in ethyl acetate (3.5 rel vol) with stirring and the mixture was cooled to 0° C. Sulfuryl chloride (0.53 mole equiv) was added in one portion, the residues were washed in with ethyl acetate (0.5 rel vol) and the mixture stirred at 0° C. for approximately 1 h. Ethyl(2-methyl-4-oxo-4,5,6,7-tetrahydro-1H-indol-1-yl)acetate (1.0 mole equiv, limiting reagent) and ethyl acetate (5 rel vol) were charged to vessel 2 and the mixture stirred at 20° C. The contents of vessel 1 were added to the mixture in vessel 2 over approximately 30 mins, washing the residues in with ethyl acetate (0.5 rel vol). Aqueous sodium carbonate (1M, 1.45 mole equiv) was added slowly (gas evolution), the mixture was stirred then the layers were allowed to separate, discarding the lower aqueous phase. A solution of sodium chloride (1.45 mole equiv) in water (5 rel vol) was added to the organic phase, the mixture was stirred then the layers allowed to separate, discarding the lower aqueous phase. The organic layer was concentrated by distillation at atmospheric pressure to around 4 rel vol. Hydroxylamine hydrochloride (1.0 mole equiv) was charged to the concentrate at 20° C. followed by tributylamine (1.0 mole equiv) and ethanol (2 rel vol) and the resulting mixture was heated at 60° C. for 4 h. The mixture was cooled to 20° C., the solid was collected by filtration, washed with ethyl acetate (2×2 rel vol) then dried at 40° C. under vacuum to provide the title compound in 87.3% yield; purity 99% w/w.

Alternative Procedure 2

In vessel 1, bis-(4-chlorobenzene)disulfide (0.53 mole equiv) was suspended in ethyl acetate (4 rel vol) with stirring and the mixture cooled to 5° C. Sulfuryl chloride (0.53 mole equiv) was added in one portion and the mixture stirred at 5° C. for approximately 1 h. Ethyl(2-methyl-4-oxo-4,5,6,7-tetrahydro-1H-indol-1-yl)acetate (1.0 equiv, limiting reagent) and ethyl acetate (5 rel vol) were charged to vessel 2 and the mixture stirred at 20° C. The contents of vessel 1 were added to the mixture in vessel 2 over approximately 30 mins, washing in the residues with ethyl acetate (0.5 rel vol). Triethylamine (1.0 mole equiv) was added and the mixture stirred overnight. The solid by product was removed by filtration, the filter cake was washed with ethyl acetate (1 rel vol) and the combined filtrates evaporated in vacuo. The residue was dissolved in a mixture of ethyl acetate (4 rel vol) and ethanol (2 rel vol) then hydroxylamine hydrochloride (1.0 mole equiv) and tributylamine (1.0 mole equiv) added. The mixture was heated at 60° C. for 4 h, then cooled to 20° C. The product was collected by filtration, washed with ethyl acetate (2×2 rel vol) then dried at 40° C. under vacuum to provide the title compound in 83% yield; purity by HPLC 95.95 area %.

Alternative Procedure 3

In vessel 1, bis-(4-chlorobenzene)disulfide (0.53 mole equiv) was suspended in ethyl acetate (4 rel vol) and cooled to 5° C. The mixture was treated with chlorine at 5° C. for 15 minutes, then purged with nitrogen and degassed under vacuum. Ethyl(2-methyl-4-oxo-4,5,6,7-tetrahydro-1H-indol-1-yl)acetate (1.0 equiv, limiting reagent) and ethyl acetate (4.5 rel vol) were charged to vessel 2 and the mixture stirred at 20° C. The contents of vessel 1 were added to the mixture in vessel 2 over approximately 30 mins, washing in the residues were with ethyl acetate (0.5 rel vol). Triethylamine (1.5 mole equiv) was added and the mixture stirred overnight. The solid by product was removed by filtration and washed with ethyl acetate (1 rel vol). Hydroxylamine hydrochloride (1.0 mole equiv) was charged to another vessel followed by the combined filtrates. Tributylamine (1.0 mole equiv) and ethanol (2 L/kg) were added and the resulting mixture was heated at 60° C. for 4 h. Further hydroxylamine hydrochloride (0.5 mole equiv) and tributylamine (0.5 mole equiv) were added then the mixture was heated at 60° C. for 4 h. The mixture was cooled to 20° C., the solid product was collected by filtration, washed with ethyl acetate (2×2 rel vol) then dried at 40° C. under vacuum to provide the title compound in 80.1% yield; purity by HPLC 96.5 area %.

Ethyl [4-acetylamino-3-(4-chlorophenylsulfanyl)-2-methyl-1H-indol-1-yl]acetate

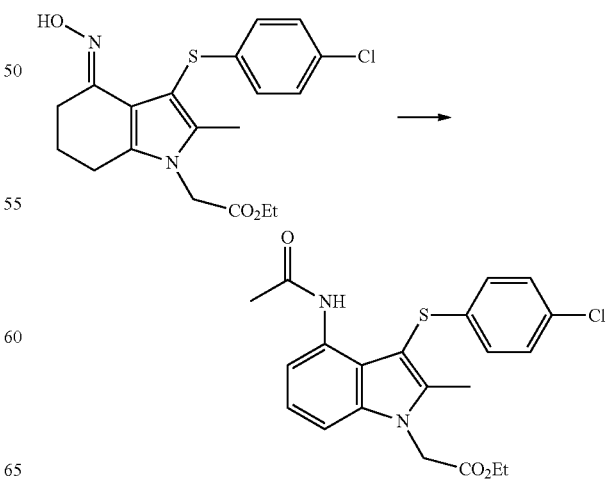

Method 1

A stirred slurry of ethyl [3-(4-chloro-phenylsulfanyl)-4-(hydroxyimino)-2-methyl-4,5,6,7-tetrahydro-1H-indol-1-yl]acetate (1.15 kg, 1.00 kg corrected for assay, 2.56 moles) and powdered NaI (191.5 g, 1.28 moles) in xylene (7.0 L) was heated to 85° C. Acetic anhydride (1.06 kg, 1.05 kg corrected for assay, 10.2 moles) was then added over 1 h at 83-85° C. The acetylated oxime is expected to be an intermediate formed in this reaction. After maintaining at this temperature for 4.5 h, the mixture was cooled to 45-50° C. and solvent was removed in vacuo (−830 to −850 mbar). Xylene (7.0 L) was added to the residue, followed by water (2.0 L), and the mixture was heated to 60° C. to give 2 clear phases. The aqueous layer was separated off, and the organic phase was concentrated in vacuo at 45-50° C. until ~10 L of distillate had been collected and crystallisation was observed in the residue. EtOH (2.0 L) was added to the residue which was then concentrated in vacuo at 45-50° C. Further EtOH (2.0 L) was added to the residue which was then cooled to 10° C. over 30 mins and held at this temperature for 1 h. The solid product was collected by filtration, washed with EtOH (1.0 L) then dried in vacuo at 40° C. for 12 h to afford crude ethyl [4-acetylamino-3-(4-chlorophenylsulfanyl)-2-methyl-1H-indol-1-yl]acetate as a solid; 0.70 kg; assay by $^1$H NMR: 96.8% w/w; 0.68 kg corrected for assay (64%); purity by HPLC: 97.9 area %. Crude ethyl [4-acetylamino-3-(4-chlorophenylsulfanyl)-2-methyl-1H-indol-1-yl]acetate (0.50 kg) was combined with the damp products from two similar preparations carried out at 2.00 kg (corrected input) scale (4.88 kg total weight) in EtOH (42.8 L) and the mixture was heated to 75° C. After holding for 15 mins at this temperature, the resulting solution was then cooled to 15° C. over 2.5 h causing crystallisation. The solid product was collected by filtration, washed on the filter with EtOH (4.76 L) then dried in vacuo at 40° C. to give the title compound as a solid; 3.25 kg; assay by $^1$H NMR 96.8% w/w; yield corrected for assay: 3.15 kg (63%); purity by HPLC: 98.6 area %; m/z: 417 (MH$^+$); $^1$H NMR: 1.12-1.24 (3H, t), 1.87 (3H, s), 2.40 (3H, s), 4.15-4.22 (2H, q), 5.23 (2H, s), 6.97-7.00 (2H, d), 7.09-7.12 (1H, m), 7.28-7.38 (3H, m), 7.48-7.51 (1H, d), 9.50 (1H, br s).

Method 2

A stirred slurry of ethyl [3-(4-chloro-phenylsulfanyl)-4-(hydroxyimino)-2-methyl-4,5,6,7-tetrahydro-1H-indol-1-yl]acetate (571 mg, 500 mg corrected for assay, 1.11 mmol) in xylene (2.5 mL) and acetic acid (2.5 ml) was heated to 107° C. Acetic anhydride (481 μl, 4.45 mmol) was then added. After heating to 95-100° C. for 2 h, analysis by HPLC indicated presence of 79 area % of ethyl [4-acetylamino-3-(4-chlorophenylsulfanyl)-2-methyl-1H-indol-1-yl]acetate in the reaction mixture (identified by comparison of retention time with a reference material).

Method 3

In flask 1, a mixture of sodium iodide (171.6 mg, 1.14 mmol) in xylene (12.5 mL), acetic acid (12.5 ml) and acetic anhydride (4.2 mL, 44.54 mmoles) was heated to 97° C. In flask 2, acetic anhydride (4.2 mL, 44.5 mmol) was added to a stirred slurry of ethyl [3-(4-chlorophenylsulfanyl)-4-(hydroxyimino)-2-methyl-4,5,6,7-tetrahydro-1H-indol-1-yl]acetate (10 g, 22.3 mmol corrected for assay) in xylene (12.5 mL) and acetic acid (12.5 ml) at ambient temperature. The mixture in flask 2 was added to the mixture in flask 1 over 2-3 hours maintaining the temperature at 97° C. The reaction was held at this temperature for a further 2 hours following the end of the addition. The reaction was cooled to 60° C. and split into 2 equal size portions. One of these portions was cooled to r.t. and propan-1-ol (25 mL) was added, following by water (25 mL), added over 15 minutes, effecting a precipitation. After stirring for 1 h, the solid product was collected by filtration, washed with propan-1-ol (2×10 mL) and dried in vacuo at 40° C. to afford crude ethyl [4-acetylamino-3-(4-chlorophenylsulfanyl)-2-methyl-1H-indol-1-yl]acetate as a solid; 4.32 g (91% based on work up of half of the reaction mixture). Purity by HPLC 97.15 area %.

Method 4

A mixture of sodium iodide (0.05 mol equiv) in xylene (1.0 rel vol), acetic acid (1.0 rel vol) and acetic anhydride (1.2 mole equiv) was heated to 97-103° C. in vessel 1 with stirring. In vessel 2, acetic anhydride (1.3 mole equiv) was added to a stirred slurry of ethyl [3-(4-chlorophenylsulfanyl)-4-(hydroxyimino)-2-methyl-4,5,6,7-tetrahydro-1H-indol-1-yl]acetate (1 mole equiv, limiting reagent) in xylene (1.0 rel vol) and acetic acid (1.0 rel vol) at 19-25° C. After stirring at this temperature for 2 h, this mixture was added to the solution in reaction vessel 1 over 2.5 h, maintaining the temperature at between 98 and 102° C. Vessel 2 was rinsed with a mixture of xylene (0.25 rel vol) and acetic acid (0.25 rel vol) which was added to vessel 1. The reaction was held at 98 to 102° C. for a further 1.5 h then cooled to 60° C. Xylene (0.9 rel vol) was added followed by a warm (60° C.) solution of sodium chloride (0.19 rel wt) in water (1.5 rel vol) and the temperature adjusted to 60° C. The aqueous layer was separated and discarded. A warm (60° C.) solution of sodium thiosulfate (0.1 mole equiv) in water (0.5 rel vol) was added and after mixing, the aqueous layer was separated and discarded. The product was precipitated by the is addition of heptanes (3 rel vol) to the organic layer, whilst maintaining the temperature at between 57 and 63° C. The resulting slurry was cooled to 20° C. over 1 h then the solid product was collected by centrifugation, washed with ethanol (3.0 rel vol) and dried to afford crude ethyl [4-acetylamino-3-(4-chlorophenylsulfanyl)-2-methyl-1H-indol-1-yl]acetate as a solid in 77% yield; purity by UHPLC 97.4 area %.

Crude ethyl [4-acetylamino-3-(4-chlorophenylsulfanyl)-2-methyl-1H-indol-1-yl]acetate (limiting reagent) was dissolved in a mixture of acetonitrile (9.1 rel vol) and water (4.5 rel vol) by heating to 80° C. with stirring. The solution was cooled to 15° C., after which the resulting solid product was collected by centrifugation, washed with ethanol (1.7 rel vol) then dried to afford ethyl [4-acetylamino-3-(4-chlorophenylsulfanyl)-2-methyl-1H-indol-1-yl]acetate as a solid in 92% yield; purity by UHPLC 99.4 area %.

Method 5

A mixture of sodium iodide (0.0625 mol equiv) in xylene (1.99 rel vol), acetic acid (0.27 rel vol) and acetic anhydride (1.27 mole equiv) was heated to 102.5° C. in vessel 1 with stirring. In vessel 2, acetic anhydride (1.27 mole equiv) was added to a stirred slurry of ethyl [3-(4-chlorophenylsulfanyl)-4-(hydroxyimino)-2-methyl-4,5,6,7-tetrahydro-1H-indol-1-yl]acetate (1 mole equiv, limiting reagent) in xylene (2.24 rel vol) and acetic acid (0.27 rel vol) at 22° C. After stirring at this temperature for 30 mins, this mixture was added to the contents of reaction vessel 1 over 50 mins maintaining the temperature at 102.5° C. The reaction was held at this temperature for a further 2.5 h. The reaction was cooled to 60° C. and sodium thiosulfate (0.05 mole equiv) and water (0.5 rel vol) were added. After mixing, and allowing the layers to separate, the lower aqueous layer was discarded then the organic layer was distilled under vacuum, removing 1.8 rel vol distillate. The temperature was adjusted to 95° C. and the product precipitated by the addition of heptanes (3 rel vol). The suspension was cooled to 20° C. over 1 h then the solid product was collected by filtration, washed with ethanol (2 rel vol) and dried in vacuo at 40° C. to afford crude ethyl [4-acetylamino-3-(4-chlorophenylsulfanyl)-2-methyl-1H-indol-1-yl]acetate as a solid; 81% yield; purity by UHPLC 98.3 area %.

Preparation and Isolation of a Sample of the Intermediate [3-[(4-chlorophenyl)sulfanyl]-1-(2-ethoxy-2-oxoethyl)-2-methyl-4,5,6,7-tetrahydro-1H-indol-4-ylidene]amino acetate Acetic anhydride (4.33 mL, 45.8 mmol) was added to a slurry of ethyl [3-(4-chlorophenylsulfanyl)-4-(hydroxyimino)-2-methyl-4,5,6,7-tetrahydro-1H-indol-1-yl]acetate (15 g, 38.2 mmol) in xylene (33.75 mL) and acetic acid (3.75 mL) and the mixture stirred at r.t. for around 20 mins. A sample of the title compound was isolated by filtration and dried at 40° C. m/z 435/437 (MH$^+$); $^1$H NMR: 7.27-7.23 (2H, m), 7.00-6.96 (2H, m), 4.92 (2H, s), 4.19 (2H, q, J=7.1 Hz), 2.68-2.59 (4H, m), 2.19 (3H, s), 1.90 (3H, s), 1.89-1.81 (2H, m), 1.22 (3H, t, J=7.1 Hz).

[4-Acetylamino-3-(4-chlorophenylsulfanyl)-2-methyl-4H-indol-1-yl]acetic acid

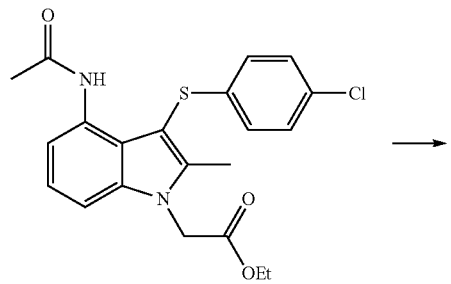

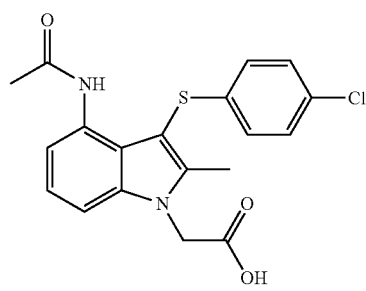

To a stirred slurry of ethyl [4-acetylamino-3-(4-chlorophenylsulfanyl)-2-methyl-1H-indol-1-yl]acetate (3.16 kg, 3.05 kg corrected for assay, 7.3 moles) in 1-propanol (15.3 L) was added aqueous NaOH (1M, 15.3 L). The mixture was then heated at 70° C. for 2 h, cooled to 40° C. then MIBK (30.5 L) was added and the mixture reheated to 80° C. Approximately 20% of the resulting biphasic mixture was removed from the reaction vessel to be processed separately. To the remainder, aqueous hydrochloric acid (1M, 13.4 L) was added to the solution over a period of 45 mins then the resulting slurry was cooled to 15° C. over 1 h and stirring continued at this temperature for a further 30 mins. The solid product was collected by filtration, washed with water (2×9.8 L) followed by EtOAc (7.3 L) then dried on the filter for 10 mins then in vacuo at 45° C. to give the title compound as a solid; 2.15 kg; assay by $^1$H NMR: 99.4% w/w; 2.14 kg corrected for assay (94%); purity: 99.5 area % by HPLC; m/z: 389 (MH$^+$); $^1$H NMR: 1.86 (3H, s), 2.34 (3H, s), 5.11 (2H, s), 6.97-7.00 (2H, d), 7.08-7.11 (1H, m), 7.27-7.30 (3H, m), 7.47-7.50 (1H, d), 9.50 (1H, br s).

Alternative Procedure 1

A mixture of ethyl [4-acetylamino-3-(4-chlorophenylsulfanyl)-2-methyl-1H-indol-1-yl]acetate (30.0 kg, 72.0 moles), 1-propanol (120.6 kg) and aqueous NaOH (1M, 150.1 kg) was heated to 68-72° C. and held at this temperature for 16 mins. The resulting solution was cooled to 18-22° C. then filtered to remove particulate matter and the filter rinsed with water (15.0 kg). MIBK (240.3 kg) was added to the combined filtrates and the bi-phasic mixture heated to 83-87° C. Aqueous hydrochloric acid (1M, 60.0 kg) was added to the hot solution over a period of around 15 mins, maintaining the reaction temperature between 83 and 87° C. followed by two further portions of the same (52.6 kg over approximately 20 mins and 52.6 kg over approximately 20 mins). The resulting slurry was cooled to between 13 and 17° C. over 2 h and stirring continued at this temperature for a further 15 mins. The solid product was collected by filtration, washed with water (2×60 kg) followed by EtOAc (81.1 kg) then dried on the filter using nitrogen at 40° C. to give the title compound as a white solid; 25.2 kg (90%)

Alternative Procedure 2

A mixture of ethyl [4-acetylamino-3-(4-chlorophenylsulfanyl)-2-methyl-1H-indol-1-yl]acetate (99.9 kg, 240 moles), ethanol (393 kg), water (450 kg) and aqueous NaOH (10M, 72.3 kg) was heated to 59-65° C. and held at this temperature for 30 mins. The resulting solution was cooled to 17-23° C. then filtered to remove particulate matter and the filter rinsed with water (50.9 kg). MIBK (403 kg) was added to the combined filtrates and the mixture heated to 55-65° C. A mixture of aqueous hydrochloric acid (10M, 65.0 kg) and water (496 kg) was added to the hot solution over a period of around 45 mins, maintaining the reaction temperature within the specified range. The resulting slurry was cooled to between 12 and 18° C. over approximately 60 mins and held at this temperature overnight. The solid product was collected by centrifugation, washed with water (396 kg) followed by ethanol (249 kg) then dried under vacuum at a maximum jacket temperature of 60° C. to give the title compound as a white solid; 79.1 kg (94%); purity: 99.5 area % by HPLC.

Scheme (IV)
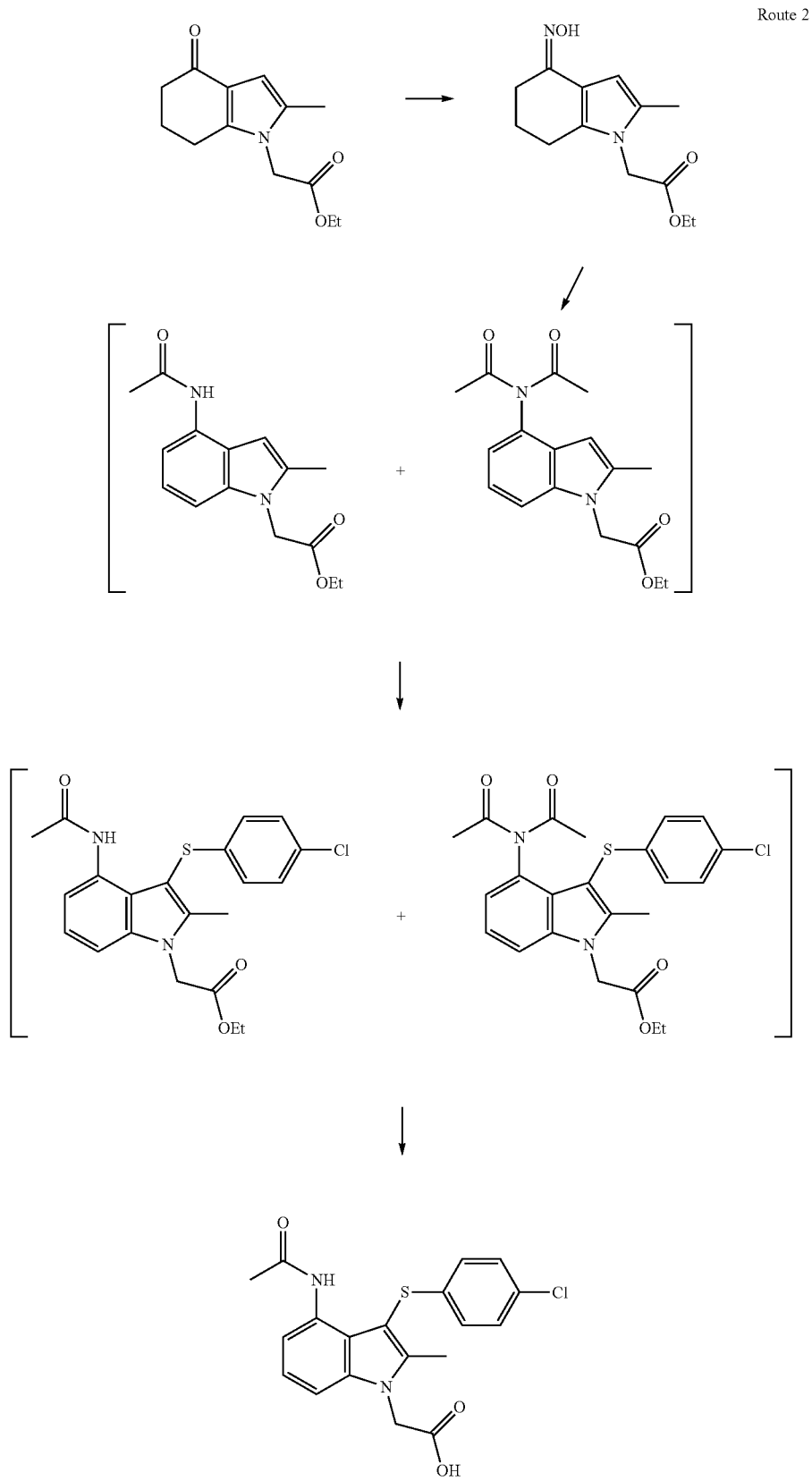
Route 2

Ethyl [4-(hydroxyimino)-2-methyl-4,5,6,7-tetrahydro-4H-indol-1-yl]acetate

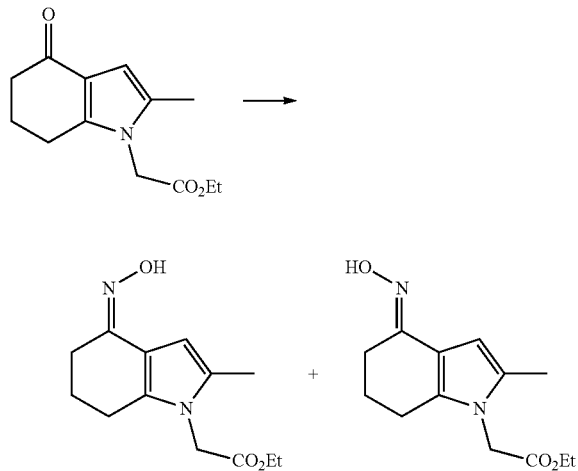

A stirred mixture of ethyl(2-methyl-4-oxo-4,5,6,7-tetrahydro-1H-indol-1-yl)acetate (59.55 g, 54.06 g corrected for purity, 0.23 moles), hydroxylamine hydrochloride (24.44 g, 23.95 g corrected for purity, 0.345 moles) and sodium acetate trihydrate (47.14 g, 46.90 g corrected for purity, 0.345 moles) in water (108 mL) and EtOH (540 mL) was heated under reflux for 2.5 h. The mixture was then cooled to 10° C., the solid product was collected by filtration then dried in vacuo at 40° C. to give the title compound as a mixture of E- and Z-isomers; 55.4 g; assay by HPLC: 99.0% w/w; yield corrected for assay: 54.8 g (95.3%); purity by HPLC: 98.9 area % as the sum of the 2 product peaks; LC-MS m/z: 250 for each of the product peaks.

[4-Acetylamino-3-(4-chlorophenylsulfamyl)-2-methyl-1H-indol-1-yl]acetic acid

A stirred mixture of ethyl [4-(hydroxyimino)-2-methyl-4,5,6,7-tetrahydro-1H-indol-1-yl]-acetate (2.068 g, 2.00 g corrected for purity, 8.0 mmol), acetic anhydride (12.37 g, 12.24 g corrected for purity, 0.120 moles) and tetrabutylammonium iodide (2.997 g, 2.953 g corrected for purity, 8.0 mmol) in xylene (16 mL) was heated under reflux for 2 h. The acetylated oxime is expected to be an intermediate formed in this reaction. After cooling to r.t. acetic anhydride and xylene were removed in vacuo at 50° C. Water (10 mL) was added to the sticky residue and the mixture was evaporated to dryness in vacuo at 50° C. After cooling to r.t., $CH_2Cl_2$ (20 mL) was added to the residue and stirring continued for 10 mins. Insoluble solid material was removed by filtration and the filtrate was concentrated in vacuo. Xylene (20 mL) was added to the residue, stirring was continued for 10 mins before some additional solid material was removed by filtration. The filtrate was concentrated in vacuo at 50° C. and EtOAc (20 mL) was added to the residue to give the product mixture as a solution in EtOAc; purity by HPLC: 9.67 area % ethyl(4-acetylamino-2-methyl-1H-indol-1-yl)acetate, and 74.79 area % ethyl(4-diacetylamino-2-methyl-1H-indol-1-yl)acetate; LC-MS showed m/z: 275 and 317, both consistent for $MH^+$.

To a solution of TCCA (0.326 g, 0.316 g corrected for purity, 1.36 mmol) in EtOAc (10 mL) was added bis(4-chlorophenyl)disulfide (1.18 g, 1.14 g corrected for purity, 4.0 mmol). The solution of ethyl(4-acetylamino-2-methyl-1H-indol-1-yl)acetate and ethyl(4-diacetylamino-2-methyl-1H-indol-1-yl)acetate prepared above was added to the mixture, dropwise, over 10 mins. After stirring for 1 h, the insoluble solid material was removed by filtration. The filtrate was concentrated in vacuo at 40° C. and EtOH (10 mL) was added to the residue to give the product mixture as a solution in EtOH; purity by HPLC: 87.47 area % as a mixture of ethyl [4-acetylamino-3-(4-chlorophenylsulfanyl)-2-methyl-1H-indol-1-yl]acetate and ethyl [3-(4-chlorophenylsulfanyl)-4-diacetylamino-2-methyl-1H-indol-1-yl]acetate; m/z: 417 and 459, both consistent for $MH^+$. A solution of NaOH (0.326 g, 0.319 g corrected for purity, 8.0 mmol) in water (10 mL) was added to the mixture of ethyl [4-acetylamino-3-(4-chlorophenylsulfanyl)-2-methyl-1H-indol-1-yl]acetate and ethyl [3-(4-chlorophenylsulfanyl)-4-diacetylamino-2-methyl-1H-indol-1-yl]acetate in EtOH prepared above. After 2 h, EtOH was removed in vacuo at 35° C. The residual aqueous layer was washed with EtOAc (10 mL), diluted with water (10 mL) then acidified to pH 4 with aqueous hydrochloric acid. The resulting product was collected by filtration then slurried in EtOH (10 mL) at 50° C. for 15 mins. After cooling back to r.t., the solid was collected by filtration, washed with EtOH (4.0 mL) then dried in vacuo at 40° C. to give the title compound as a solid; 1.1 g (35.4% over 3 steps); purity by HPLC: 98.24 area %.

Scheme (V)

Route 3

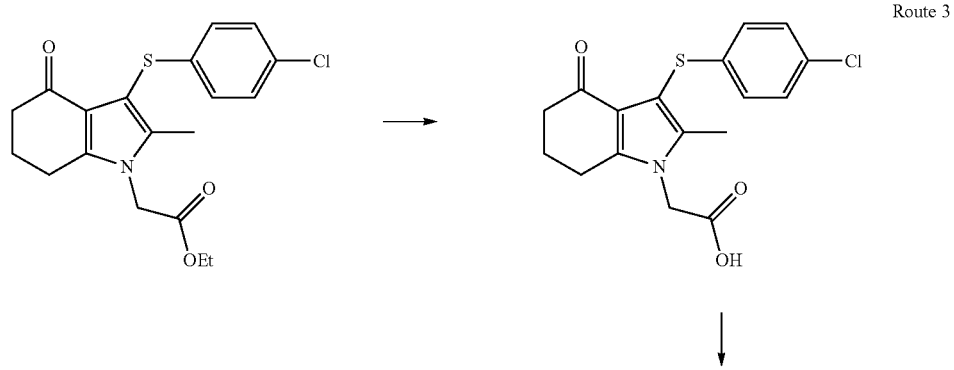

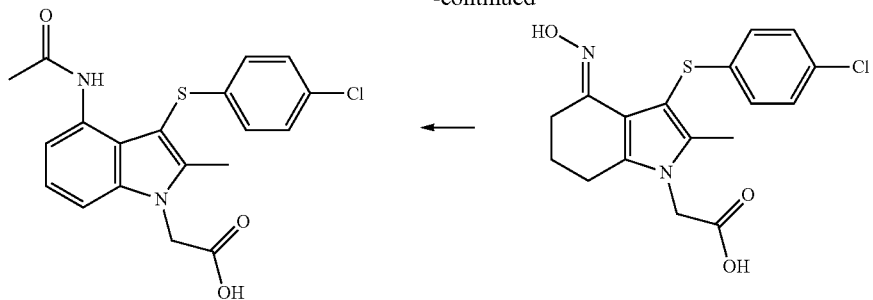

[3-(4-Chlorophenylsulfanyl)-2-methyl-4-oxo-4,5,6,7-tetrahydro-1H-indol-1-yl]acetic acid

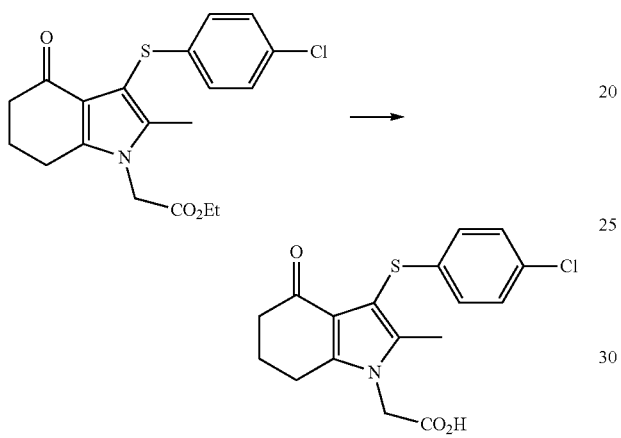

A solution of LiOH (1.79 g, 1.77 g corrected for assay, 42.2 mmol) was added to a stirred solution of ethyl [3-(4-chlorophenylsulfanyl)-2-methyl-4-oxo-4,5,6,7-tetrahydro-1H-indol-1-yl]acetate (7.5 g, 5.33 g corrected for assay, 14.1 mmol) in a mixture of THF (27 mL) and MeOH (27 mL). The mixture was stirred for 1 h. The solvents were removed in vacuo (45 mbar) at 45° C. until the volume of the mixture was ~20 mL. Water (27 mL) and CH$_2$Cl$_2$ (27 mL) was added and the mixture stirred for 5 mins. The layers were allowed to separate, concentrated aqueous hydrochloric acid (5 mL) was added to the aqueous layer and the resulting solid product was collected by filtration and washed with water (5 mL). This crude damp product was slurried in a mixture of EtOAc (20 mL), CH$_5$Cl$_2$ (20 mL) and heptane (20 mL) at r.t. The product was dried briefly on the filter to give the title compound; 4.64 g; assay by $^1$H NMR: 89.3% w/w; yield corrected for assay: 4.14 g (84%); purity by LC 99.1 area %; m/z: 350 (MH$^+$); $^1$H NMR: 1.99-2.05 (2H, m), 2.16 (3H, s), 2.26-2.31 (2H, t), 2.73-2.77 (2H, t), 4.83 (2H, s), 6.95-6.99 (2H, d), 7.23-7.27 (2H, d).

Route 3A

Alternative Synthesis of [3-(4-Chlorophenylsulfanyl)-2-methyl-4-oxo-4,5,6,7-tetrahydro-1H-indol-1-yl]acetic acid

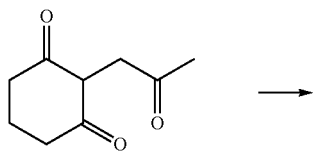

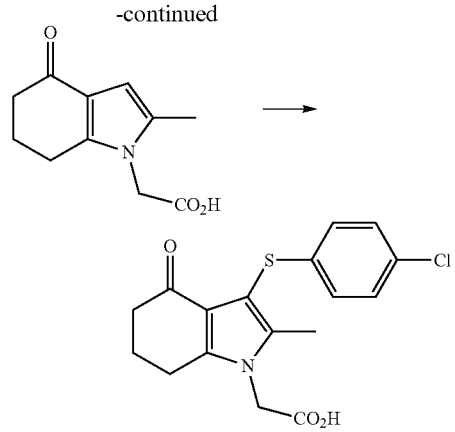

2-(2-methyl-4-oxo-4,5,6,7-tetrahydro-1H-indol-1-yl) acetic acid

A stirred mixture of 2-(2-oxopropyl)cyclohexane-1,3-dione (prepared by evaporation of an ethanolic solution to dryness under vacuum) (20.0 g, 119 mmol) and glycine (17.9 g, 238 mmol) in acetic acid (100 mL) was heated under reflux for 1.5 h then allowed to cool to r.t. Water (100 mL) was then added and the mixture evaporated to a thick oil in vacuo. Acetone (200 mL) and water (40 mL) were added to the residue and the mixture stirred for 30 mins at r.t., after which the solid was collected by filtration and the filtrates retained. The solid was slurried with further acetone (100 mL) and water (20 mL) at r.t. then removed by filtration. The combined filtrates were concentrated in vacuo then dissolved in aqueous sodium hydroxide (1M, 200 mL), adding a small amount of 10M sodium hydroxide to bring the pH to 14. After washing with ethyl acetate (2×100 mL), the mixture was acidified by the addition of aqueous hydrochloric acid (5M, 60 mL) then sodium chloride (50 g) was added. After stirring for 4 h, the solid product was collected by filtration, washed with acetone (2×25 mL) then dried under vacuum at 40° C. to afford the title compound as an orange-brown solid; 7.45 g (30%); purity 99.1 area % by HPLC; m/z: 208 (MH$^+$); $^1$H-NMR: 13.2 (1H, br s), 6.02 (1H, s), 4.67 (2H, s), 2.65 (2H, t, J=6.2 Hz), 2.29-2.24 (2H, m), 2.10 (3H, s), 2.02-1.95 (2H, m).

[3-(4-Chlorophenylsulfanyl)-2-methyl-4-oxo-4,5,6,7-tetrahydro-1H-indol-1-yl]acetic acid

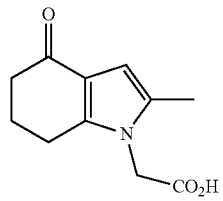

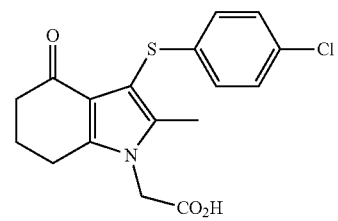

Sulfuryl chloride (0.2 mL, 2.5 mmol) was added slowly with stirring to a solution of bis-(4-chlorobenzene)disulfide (0.72 g, 2.5 mmol) in ethyl acetate (7.5 mL) in reaction flask 1 at r.t. On completion of the addition, the mixture was allowed to stir for a further 60 mins. The contents of reaction flask 1 were then added over a period of 5 mins to a stirred suspension of 2-(2-methyl-4-oxo-4,5,6,7-tetrahydro-1H-indol-1-yl)acetic acid (0.9 g, 4.3 mmol) in ethyl acetate (7.5 mL) in reaction flask 2 at r.t. Reaction flask 1 was rinsed with ethyl acetate (2 mL) which was transferred into reaction flask 2. Stirring was continued for 1 h then the reaction was quenched by the addition of water (15 mL). After leaving overnight, aqueous sodium hydroxide (1M, 25 mL) was added to the biphasic mixture with stirring followed by a small amount of 10M sodium hydroxide to bring the pH to 14. The layers were separated, the aqueous phase was washed with ethyl acetate (25 mL), then acidified using aqueous hydrochloric acid (5M, 7 ml). After stirring at r.t., the oil which had initially separated out solidified and was collected by filtration, then washed with water (2×10 mL) and dried under vacuum at 40° C. to leave the title compound as a pale brown solid; 1.0 g (66%); purity: 79.5 area % by HPLC; m/z: 350/352 (MH$^+$); $^1$H-NMR: 13.3 (1H, br s), 7.25 (2H, d, J=8.3 Hz), 6.96 (2H, d, J=8.3 Hz), 4.84 (2H, s), 2.75 (2H, t, J=5.9 Hz), 2.28 (2H, t, J=6.1 Hz), 2.16 (3H, s), 2.03-1.97 (2H, m).

[3-(4-Chlorophenylsulfanyl)-4-(hydroxyimino)-2-methyl-4,5,6,7-tetrahydro-4H-indol-1-yl]acetic acid

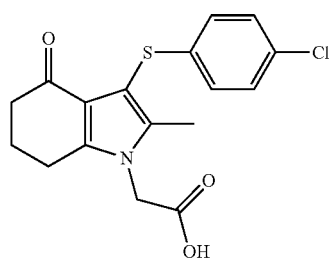

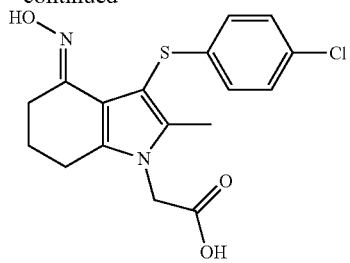

A mixture of [3-(4-chlorophenylsulfanyl)-2-methyl-4-oxo-4,5,6,7-tetrahydro-1H-indol-1-yl]acetic acid (4.0 g, 3.57 g corrected for assay, 10.2 mmol), hydroxylamine hydrochloride (1.05 g, 1.04 g corrected for assay, 15.0 mmol) and anhydrous sodium acetate (1.24 g, 1.23 g corrected for assay, 15.0 mmol) in EtOH (40 mL) was heated under reflux for 6 h. After cooling to 0° C., the solid product was collected by filtration then slurried in a mixture of EtOH (14 mL) and water (14 mL) for 15 mins at r.t. The solid was collected by filtration, washed with acetone (14 mL) then dried on the filter to give the title compound; 3.42 g; assay by NMR: 95.3% w/w; yield corrected for assay: 3.26 g (87%); m/z: 365 (MH$^+$); 1.79-1.83 (2H, m), 2.13 (3H, s), 2.54-2.59 (4H, t), 4.73 (2H, s), 6.91-6.98 (2H, d), 7.20-7.25 (2H, d), 10.23 (1H, br s).

Alternative Synthesis of [3-(4-Chlorophenylsulfanyl)-4-(hydroxyimino)-2-methyl-4,5,6,7-tetrahydro-1H-indol-1-yl]acetic acid

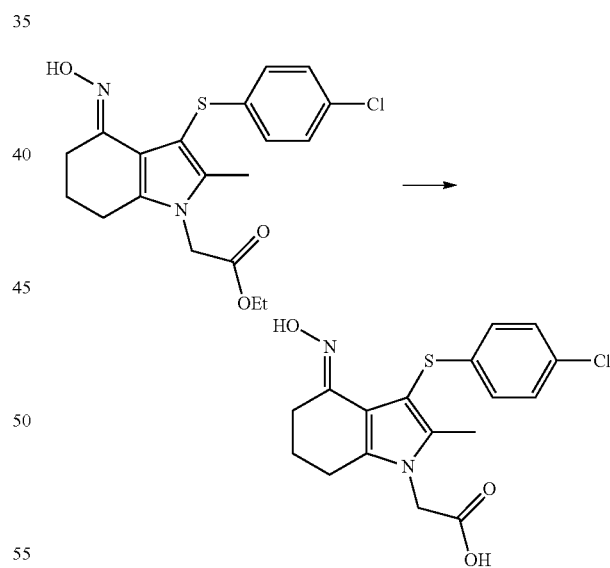

Aqueous sodium hydroxide (1M, 10 mL, 10 mmol) and water (20 mL) were added to a stirred suspension of ethyl [3-(4-chloro-phenylsulfanyl)-4-(hydroxyimino)-2-methyl-4,5,6,7-tetrahydro-1H-indol-1-yl]acetate (4.0 g, 10.2 mmol) and ethanol 40 mL) and the mixture was warmed up to 40° C. After 1.5 h at this temperature, the reaction mixture was allowed to cool to r.t. and held overnight. The suspension was reheated to 33° C. and acetic acid (1.7 mL, 29.7 mmol) added to the resulting solution. The mixture was allowed to cool to r.t., the solid product was collected by filtration, washed with water (2×20 mL), then dried under vacuum at 30° C. to provide the title compound as a solid; 2.94 g (79%); purity by HPLC 98.9 area %

[4-Acetylamino-3-(4-chlorophenylsulfanyl)-2-methyl-1H-indol-1-yl]acetic acid

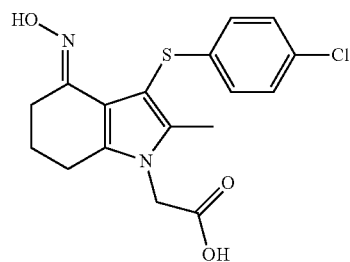

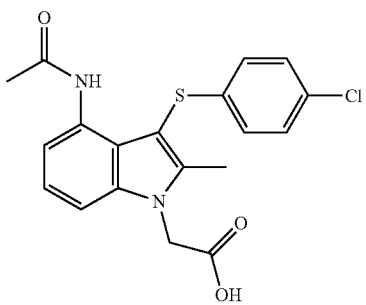

A mixture of [3-(4-chloro-phenylsulfanyl)-4-(hydroxyimino)-2-methyl-4,5,6,7-tetrahydro-1H-indol-1-yl]acetic acid (1.0 g, 0.9 g corrected for assay, 2.6 mmol), NaI (0.20 g, 1.3 mmol) and acetic anhydride (1.0 mL, 10.6 mmol) in xylene (6.7 mL) was heated at 85° C. for 5 h. The acetylated oxime is expected to be an intermediate formed in this reaction. After cooling to r.t., a sample was analysed by HPLC-MS showing 39 area % [4-acetylamino-3-(4-chlorophenylsulfanyl)-2-methyl-1H-indol-1-yl]acetic acid, at a is retention time consistent with an authentic sample.

Synthesis of 2-(4-acetamido-2-methyl-1H-indol-1-yl)acetic acid

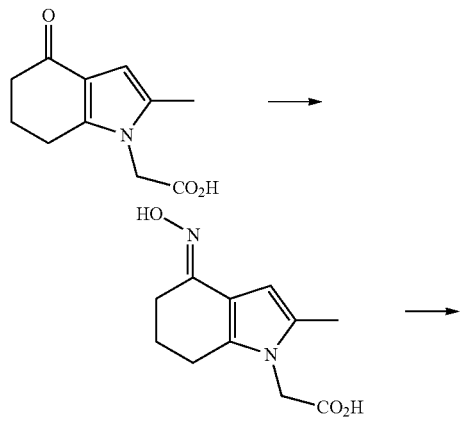

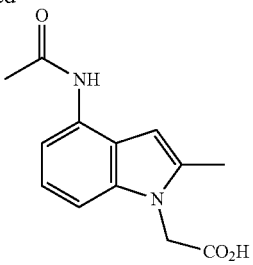

2-[4-(hydroxyimino)-2-methyl-4,5,6,7-tetrahydro-1H-indol-1-yl]acetic acid

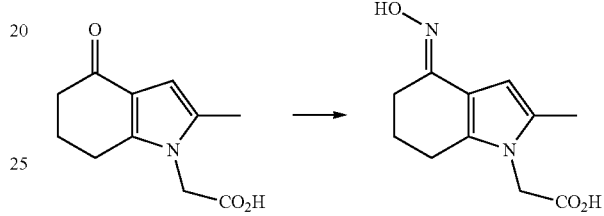

A mixture of 2-(2-methyl-4-oxo-4,5,6,7-tetrahydro-1H-indol-1-yl)acetic acid (4.0 g, 19 mmol), hydroxylamine hydrochloride (2.0 g, 29 mmol) and anhydrous sodium acetate (2.4 g, 29 mmol) in ethanol (40 mL) was heated under reflux for 6 h with stirring. After cooling to r.t. and holding overnight, the mixture was further cooled to 4° C. The solid product was collected by filtration, washed with water (15 mL) followed by ethanol (15 mL) then dried under vacuum at 40° C. to afford the title compound as a pale brown solid; 3.68 g (86%); purity: 96.7 area % by HPLC; m/z: 223 (MH$^+$); $^1$H-NMR: 9.82 (1H, br s), 6.48 (1H, d, J=0.90 Hz), 4.58 (2H, s), 2.56-2.51 (2H, m), 2.29-2.24 (2H, m), 2.09 (3H, s), 1.86-1.79 (2H, m).

2-(4-Acetamido-2-methyl-1H-indol-1-yl)acetic acid

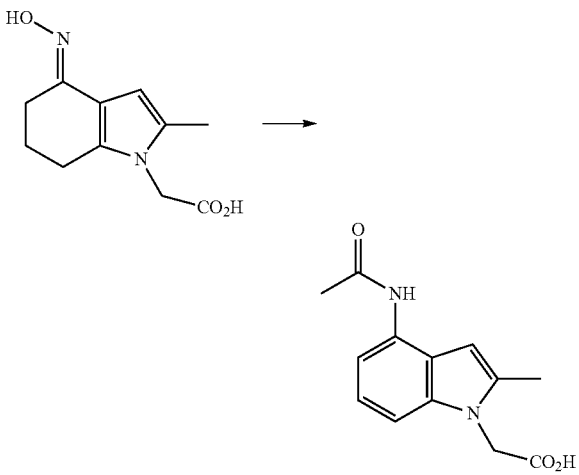

Acetic anhydride (1.0 mL, 10.6 mmol) was added to a stirred slurry of 2-[4-(hydroxyimino)-2-methyl-4,5,6,7-tetrahydro-1H-indol-1-yl]acetic acid (2.0 g, 9.0 mmol) in a mixture of acetic acid (10 mL) and xylene (10 mL) at r.t. in reaction flask 1 (mildly exothermic addition) then the mixture was held with stirring for 75 mins. Meanwhile, reaction flask 2 was charged with acetic acid (5 mL), xylene (5 mL), acetic anhydride (2.6 mL, 27.5 mmol), and sodium iodide (270 mg, 1.80 mmol) and the mixture was heated to 90-100° C. with stirring. The contents of reaction flask 1 were transferred to reaction flask 2 in aliquots over a period of 1.5 h, whilst maintaining the reaction temperature at 90-100° C. Reaction flask 1 was rinsed with a mixture of xylene (2 mL) and acetic acid (2 mL) which was transferred into reaction flask 2. Subsequently, the reaction mixture was maintained at 100° C. for a further 2.5 h and was then allowed to cool to r.t. The liquid phase was decanted off from a thick residue in the reaction flask and the residue was washed with acetic acid (5 mL) followed by xylene (5 mL). The decanted liquid and washes were combined and evaporated to dryness in vacuo to leave a dark brown residue. Analysis by HPLC and LC-MS showed 29.2 area % of a peak giving m/z 247 (MH$^+$).

Scheme (VI)

Route 4

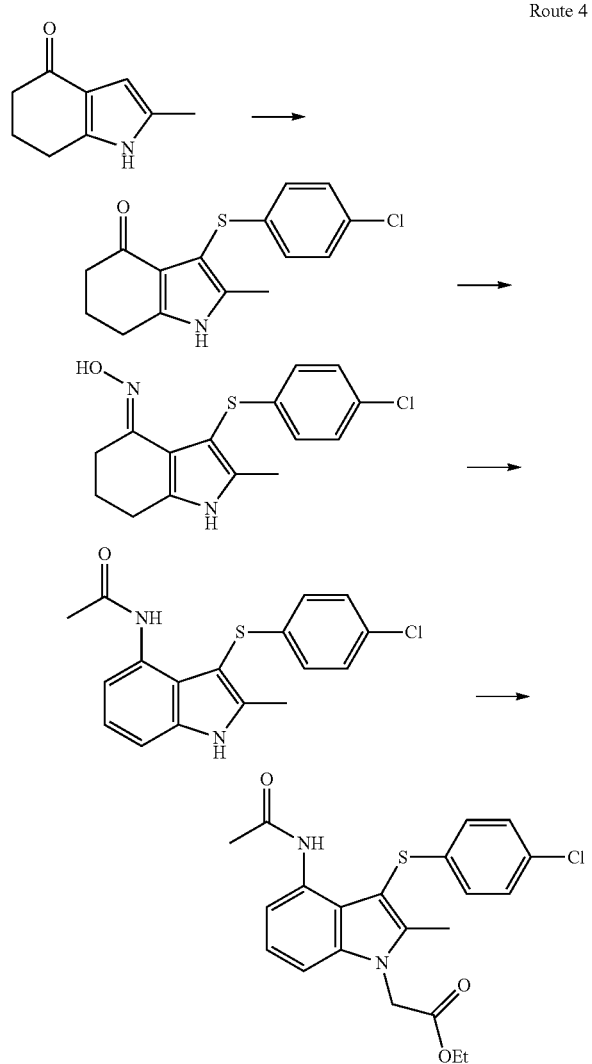

3-(4-Chlorophenylsulfanyl)-2-methyl-4,5,6,7-tetrahydro-1H-indol-4-one

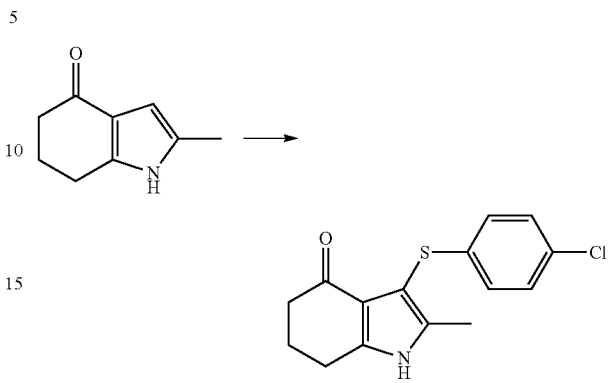

Sulfuryl chloride (1.7 mL, 21 mmol) was added slowly with stirring to a solution of bis-(4-chlorobenzene)disulfide (6.0 g, 21 mmol) in ethyl acetate (45 mL) in reaction flask 1, which was cooled in an ice-water bath. On completion of the addition, the mixture was allowed to stir at r.t. for 30 mins. The contents of reaction flask 1 were then added over a period of 1 h to a stirred suspension of 2-methyl-4,5,6,7-tetrahydro-1H-indol-4-one (5.0 g, 33.5 mmol) in ethyl acetate (22.5 mL) in reaction flask 2, cooled in an ice-water bath, adding further ethyl acetate during the course of the addition to keep the heterogeneous reaction mixture mobile. Reaction flask 1 was rinsed with ethyl acetate (10 mL) which was transferred into reaction flask 2. Stirring was continued overnight whilst the thick, heterogeneous mixture was allowed to warm to r.t. The solid product was collected by filtration, washed with ethyl acetate (2×15 mL) then dried under vacuum at 40° C. to provide the title compound as a pale yellow solid; 8.62 g (88%); purity: 94.3 area % by HPLC; m/z: 292/294 (MH$^+$); $^1$H-NMR: 11.77 (1H, s), 7.24 (2H, d, J=8.1 Hz), 6.95 (2H, d, J=8.1 Hz), 2.80-2.74 (2H, m), 2.29-2.21 (2H, m), 2.16 (3H, s), 2.05-1.95 (2H, m).

N-[-3-(4-chlorophenylsulfanyl)-2-methyl-4,5,6,7-tetrahydro-1H-indol-4-ylidene]hydroxylamine

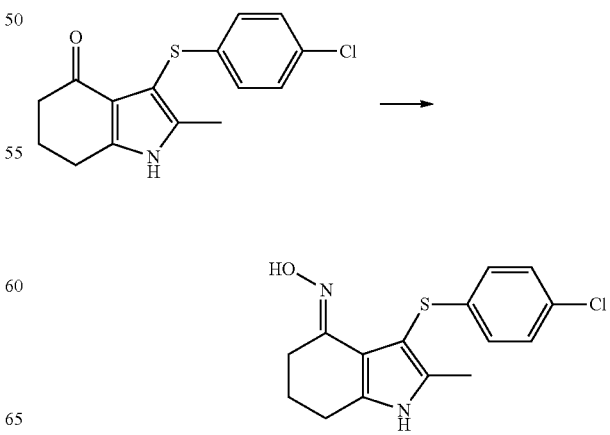

Tributylamine (6.6 mL 28 mmol) was added to a stirred suspension of 3-(4-chlorophenylsulfanyl)-2-methyl-4,5,6,7-tetrahydro-1H-indol-4-one (8.0 g, 27 mmol) and hydroxylamine hydrochloride (1.9 g, 27 mmol) in ethanol (40 mL). The mixture was heated to 65° C. and maintained at this temperature for 4 h then allowed to cool to r.t. and left overnight. Additional hydroxylamine hydrochloride (0.15 g, 2.2 mmol) and tributylamine (1.0 mL, 4.2 mmol) were added and the mixture was re-heated to 65° C. for a further 2 h. After cooling to r.t., the solid product was collected by filtration, washed with ethanol (2×10 mL) then dried in a vacuum oven at 40° C. to give the title compound as an off-white solid; 5.71 g (68%); purity: 96.3 area % by HPLC; m/z: 307/309 (MH$^+$); $^1$H-NMR: 11.26 (1H, s), 10.20 (1H, s), 7.23 (2H, m), 6.92 (2H, m), 2.62-2.58 (2H, m), 2.56-2.52 (2H, m), 2.12 (3H, s), 2.83-1.76 (2H, m).

N-[3-(4-chlorophenylsulfanyl)-2-methyl-1H-indol-4-yl]acetamide

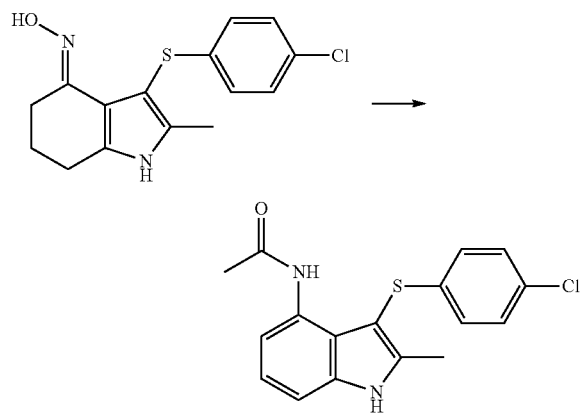

Acetic anhydride (1.1 mL, 11.6 mmol) was added to a stirred slurry of N-[-3-(4-chlorophenylsulfanyl)-2-methyl-4,5,6,7-tetrahydro-1H-indol-4-ylidene]hydroxylamine (3.0 g, 9.8 mmol) in a mixture of acetic acid (15 mL) and xylene (15 mL) at r.t. in reaction flask 1 (mildly exothermic addition) then the mixture was held with stirring for 45 mins. Meanwhile, reaction flask 2 was charged with acetic acid (7.5 mL), xylene (7.5 mL), acetic anhydride (1.1 mL, 11.6 mmol), and sodium iodide (70 mg, 0.47 mmol) and the mixture was heated to 110° C. with stirring. The contents of reaction flask 1 were transferred to reaction is flask 2 in aliquots over a period of 2 h, whilst maintaining the reaction temperature at 110° C. Reaction flask 1 was rinsed with a mixture of xylene (2 mL) and acetic acid (2 mL) which was transferred to reaction flask 2. Subsequently, the reaction mixture was maintained at 110° C. for a further 3 h then allowed to cool to r.t. and held overnight. The reaction mixture was evaporated to dryness in vacuo to leave a dark brown solid residue. This was purified by chromatography on silica gel, eluting with dichloromethane/ethyl acetate to provide the title compound as an off-white solid; 2.74 g (85%); purity 95.6 area % by HPLC; m/z: 331/333 (MH$^+$); $^1$H-NMR: 11.84 (1H, s), 9.45 (1H, s), 7.45 (1H, d, J=7.7 Hz), 7.29 (2H, d, J=8.3 Hz), 7.17 (1H, d, J=8.0 Hz), 7.04 (1H, t, J=7.9 Hz), 6.98 (2H, d, J=8.2 Hz), 2.40 (3H, s), 1.84 (3H, s).

Ethyl [4-acetylamino-3-(4-chlorophenylsulfanyl)-2-methyl-1H-indol-1-yl]acetate

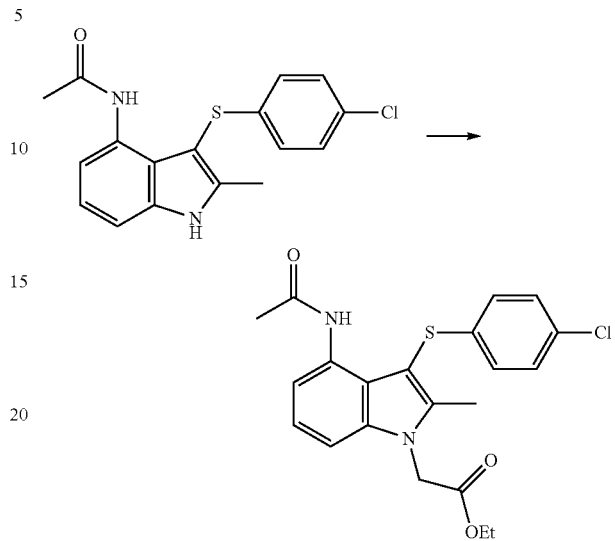

A mixture of N-[3-(4-chlorophenylsulfanyl)-2-methyl-1H-indol-4-yl]acetamide (1.0 g, 3.0 mmol), anhydrous potassium carbonate (0.63 g, 4.6 mmol), acetone (10 mL) and ethyl bromoacetate (0.50 mL, 4.5 mmol) was heated under reflux for 1.5 h then cooled to r.t. and left stirring at this temperature overnight. After heating under reflux for an additional 1 h, the mixture was cooled to r.t. Water (2×10 mL) was added, the solid product was collected by filtration, washed with water (10 mL), then dried in a vacuum oven at 40° C. to afford the title compound as an off-white solid; 1.16 g (92%); purity 95.4 area % by HPLC; m/z: 417/419 (MH$^+$); $^1$H-NMR: 9.52 (1H, s), 7.45 (1H, d, J=7.9 Hz), 7.33 (1H, d, J=8.2 Hz), 7.29 (2H, d, J=8.6 Hz), 7.11 (1H, t, J=8.0 Hz), 6.97 (1H, d, J=8.6 Hz), 5.24 (2H, s), 4.18 (2H, q, J=7.1 Hz), 2.39 (3H, s), 1.86 (3H, s), 1.22 (3H, t, J=7.1 Hz).

The invention claimed is:
1. A compound of formula (X):

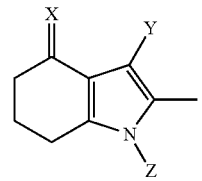

wherein:
X is =O, =N—OH or =N—OC(O)Me;
Y is hydrogen or

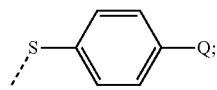

Q is hydrogen or chloro; and
Z is hydrogen or —CH$_2$COOR$^1$ wherein R$^1$ is selected from hydrogen, optionally substituted hydrocarbyl and optionally substituted heterocyclyl;
provided that when Y is hydrogen, Z is not hydrogen or a salt thereof.

2. A compound according to claim 1 of formula (II):

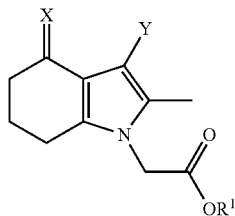

(II)

wherein:
R¹ is selected from hydrogen, optionally substituted hydrocarbyl and optionally substituted heterocyclyl;
X is =O, =N—OH or =N—OC(O)Me;
Y is hydrogen or

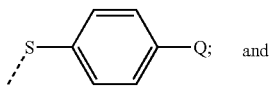

and

Q is hydrogen or chloro;
or a salt thereof.

3. The compound of formula (II), or a salt thereof, as claimed in claim 2, wherein:
R¹ is selected from hydrogen, $C_{1-6}$alkyl, $C_{2-6}$alkenyl, $C_{2-6}$alkynyl, $C_{3-6}$cycloalkyl, optionally substituted phenyl and optionally substituted benzyl.

4. The compound of formula (II), or a salt thereof, as claimed in claim 2, wherein:
R¹ is selected from hydrogen, $C_{1-6}$alkyl, $C_{2-6}$alkenyl, $C_{2-6}$alkynyl, $C_{3-6}$cycloalkyl, phenyl and benzyl; wherein the phenyl and benzyl are optionally substituted by one or more halo, nitro, cyano, hydroxy, $C_{1-6}$alkyl, $C_{1-6}$alkoxy, $C_{1-6}$alkanoyl, N—($C_{1-6}$alkyl)amino, N,N—($C_{1-6}$alkyl)$_2$-amino, N—($C_{1-6}$alkanoyl)amino, N—($C_{1-6}$alkanoyl)-N—($C_{1-6}$alkyl)amino, carbamoyl, sulfamoyl, N—($C_{1-6}$-alkyl)carbamoyl, N,N—($C_{1-6}$alkyl)$_2$-carbamoyl, N—($C_{1-6}$alkyl)sulfamoyl, N,N—($C_{1-6}$alkyl)$_2$sulfamoyl or ($C_{1-6}$alkyl)-S(O)$_a$— wherein a is 0-2.

5. The compound of formula (II), or a salt thereof, as claimed in claim 2, wherein:
R¹ is selected from $C_{1-6}$alkyl, $C_{2-6}$alkenyl, $C_{2-6}$alkynyl, $C_{3-6}$cycloalkyl, phenyl and benzyl.

6. The compound of formula (II), or a salt thereof, as claimed in claim 2, wherein Y is hydrogen.

7. The compound of formula (II), or a salt thereof, as claimed in claim 2, wherein Y is 4-chlorophenylsulfanyl.

8. The compound of formula (II), or a salt thereof, as claimed in claim 2, wherein X is =O.

9. The compound of formula (II), or a salt thereof, as claimed in claim 2, wherein X is =N—OH.

10. A compound according to claim 1, which is of formula (XI):

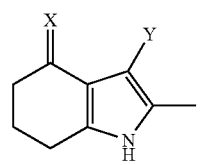

wherein:
X is =O, =N—OH or =N—OC(O)Me;
Y is

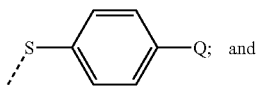

and

Q is hydrogen or chloro;
or a salt thereof.

11. The compound of formula (XI), or salt thereof, as claimed in claim 10, wherein Y is 4-chlorophenylsulfanyl.

12. The compound of formula (XI), or salt thereof, as claimed in claim 10, wherein X is =O or =N—OH.

13. A process comprising reaction of a compound of formula (II) of formula (IIc):

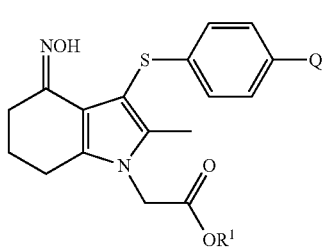

(IIc)

with an acetylating agent;
wherein the values of R¹ are as defined in claim 1, and wherein Q is chloro.

14. A process comprising the reaction of a compound of formula (II) of formula (IId):

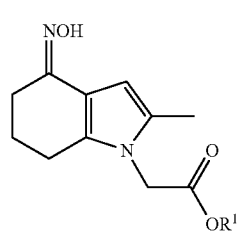

(IId)

with an acetylating agent;
wherein R¹ is as defined in claim 1.

15. The process as claimed in claim 13 or claim 14 wherein the acetylating agent is acetic anhydride.

16. The process as claimed in claim 13 or 14, wherein the reaction is carried out in the presence of an iodide salt.

17. The process as claimed in claim 13 or 14, wherein the reaction is carried out in the presence of a Lewis acid.

18. The process as claimed in claim 13 or 14, wherein the reaction is carried out in the presence of a carboxylic acid co-solvent.

19. A process for the preparation of a compound of formula (I):

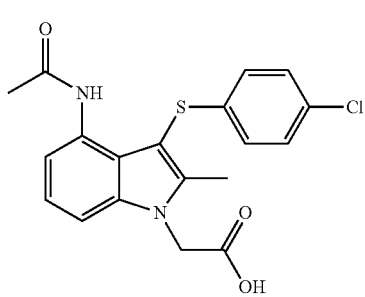

(I)

which comprises reaction of a compound of formula (IIAA):

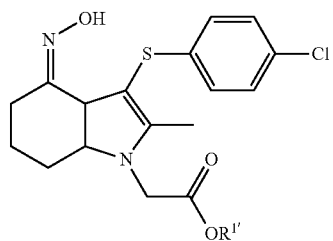

(IIAA)

where $R^{1'}$ is hydrogen or $C_{1-6}$alkyl with an acylating agent followed by de-esterification.

20. A process according to claim 19 in which $R^{1'}$ hydrogen or ethyl.

21. A process according to claim 19 in which the acylating agent is acetic anhydride.

22. A process according to claim 19 which is carried out in the presence of xylene and sodium iodide.

\* \* \* \* \*

UNITED STATES PATENT AND TRADEMARK OFFICE
CERTIFICATE OF CORRECTION

PATENT NO. : 8,227,622 B2  
APPLICATION NO. : 12/830577  
DATED : July 24, 2012  
INVENTOR(S) : Debra Ainge et al.

Page 1 of 1

It is certified that error appears in the above-identified patent and that said Letters Patent is hereby corrected as shown below:

Col. 43, line 39, "$(C_{1-6}alkyl)_2$-amino," should read -- $(C_{1-6}alkyl)_2amino$, --.

Col. 43, line 41, "N-$(C_{1-6}$-alkyl)" should read -- N-$(C_{1-6}alkyl)$ --.

Col. 46, line 3, "hydrogen" should read -- is hydrogen --.

Signed and Sealed this  
Sixteenth Day of October, 2012

David J. Kappos  
*Director of the United States Patent and Trademark Office*